(12) United States Patent
Murakoshi et al.

(10) Patent No.: US 9,001,969 B2
(45) Date of Patent: Apr. 7, 2015

(54) RADIATION IMAGING SYSTEM

(75) Inventors: Dai Murakoshi, Kanagawa (JP); Takuji Tada, Kanagawa (JP); Toshitaka Agano, Kanagawa (JP); Kenji Takahashi, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 448 days.

(21) Appl. No.: 13/522,010

(22) PCT Filed: Feb. 2, 2011

(86) PCT No.: PCT/JP2011/052675
§ 371 (c)(1),
(2), (4) Date: Jul. 12, 2012

(87) PCT Pub. No.: WO2011/096584
PCT Pub. Date: Aug. 11, 2011

(65) Prior Publication Data
US 2012/0288056 A1    Nov. 15, 2012

(30) Foreign Application Priority Data

Feb. 4, 2010   (JP) ................. 2010-022730
Sep. 22, 2010  (JP) ................. 2010-211860
Nov. 30, 2010  (JP) ................. 2010-267588

(51) Int. Cl.
*G01N 23/00*    (2006.01)
*G01N 23/04*    (2006.01)
(Continued)

(52) U.S. Cl.
CPC .............. *A61B 6/484* (2013.01); *A61B 6/4233* (2013.01); *A61B 6/5241* (2013.01);
(Continued)

(58) Field of Classification Search
CPC .... A61B 6/484; A61B 6/4291; A61B 6/4035; A61B 6/588; G21K 2207/005; G21K 2201/06; G21K 1/06; G21K 1/067

USPC ................ 378/37, 41, 62, 70, 71, 85–87
See application file for complete search history.

(56) References Cited

U.S. PATENT DOCUMENTS 6,282,264 B1 *  8/2001  Smith et al. ............. 378/189
7,522,698 B2 *  4/2009  Popescu et al. ............ 378/19
(Continued)

FOREIGN PATENT DOCUMENTS

CN         101532969 A     9/2009
JP         2008-545981 A   12/2008
WO         2008/102654 A1  8/2008

OTHER PUBLICATIONS

International Search Report in PCT/JP2011/052675 dated Mar. 15, 2011 (English Translation Thereof).
(Continued)

*Primary Examiner* — Jack Berman
*Assistant Examiner* — Kevin Chung
(74) *Attorney, Agent, or Firm* — McGinn IP Law Group, PLLC.

(57) ABSTRACT

An X-ray imaging system is provided with an X-ray source (11), first and second absorption gratings (31, 32), and a flat panel detector (FPD) (30), and obtains a phase contrast image of an object H by performing imaging while moving the second absorption grating (32) in x direction relative to the first absorption grating (31). The following mathematical expression is satisfied where $p_1'$ denotes a period of a first pattern image at a position of the second absorption grating (32), and $p_2'$ denotes a substantial grating pitch of the second absorption grating (32), and $D_X$ denotes a dimension, in the x-direction, of an X-ray imaging area of each pixel of the FPD (30). Here, "n" denotes a positive integer.

$$D_X \neq n \times (p_1' \times p_2')/|p_1' - p_2'|$$

29 Claims, 27 Drawing Sheets

(51) Int. Cl.
*A61B 6/02* (2006.01)
*A61B 6/00* (2006.01)
*G21K 1/06* (2006.01)
*A61B 6/03* (2006.01)
*A61B 6/06* (2006.01)

(52) U.S. Cl.
CPC ............ *A61B 6/4291* (2013.01); *G21K 1/067* (2013.01); *G21K 1/06* (2013.01); *G21K 2201/06* (2013.01); *A61B 6/022* (2013.01); *A61B 6/03* (2013.01); *A61B 6/06* (2013.01); *A61B 6/4441* (2013.01); *A61B 6/4464* (2013.01); *A61B 6/502* (2013.01); *G21K 2207/005* (2013.01)

(56) References Cited

U.S. PATENT DOCUMENTS 8,451,975 B2 * 5/2013 Tada ............................... 378/87
2007/0183562 A1 * 8/2007 Popescu et al. ................ 378/19
2007/0183583 A1 * 8/2007 Baumann et al. ............ 378/145
2009/0092227 A1 4/2009 David et al.

OTHER PUBLICATIONS

C. David et al., "Differential X-ray phase contrast imaging using a shearing interferometer", Applied Physics Letters, vol. 81, No. 17, Oct. 2002, p. 3287.
Hector Canabal et al., "Improved phase-shifting method for automatic processing of moiré deflectograms", Applied Optics, vol. 37, No. 26, Sep. 1998, p. 6227.
Chinese Office Action dated May 26, 2014 with an English translation thereof.
Supplementary European Search Report dated, Jul. 8, 2013.

* cited by examiner

90° ROTATION

RADIATION IMAGING SYSTEM

TECHNICAL FIELD

The present invention relates to a radiation imaging system for capturing an image of an object using radiation such as X-ray, and more particularly to a radiation imaging system for performing phase imaging of an object.

BACKGROUND ART

Because X-ray attenuates depending on an atomic number of an element constituting a substance and density and thickness of the substance, it is used as a probe for inspecting the inside of an object. X-ray imaging is widely used in medical diagnoses and non-destructive inspections.

In a general X-ray imaging system, an object is arranged between an X-ray source, for emitting X-ray, and an X-ray image detector, for detecting the X-ray, to capture an X-ray transmission image of the object. Each X-ray emitted from the X-ray source to the X-ray image detector is attenuated (absorbed) by an amount depending on the difference in object's properties (atomic number, density, thickness) existing on an X-ray path to the X-ray image detector. As a result, an X-ray absorption contrast image of the object is detected by the X-ray image detector and imaged or visualized. Photostimulable phosphor, and a flat panel detector (FPD) using a semiconductor circuit are widely used in addition to a combination of an X-ray intensifying screen and a film.

The X-ray absorption properties decrease as the atomic number of an element constituting a substance decreases. This causes a problem that in vivo soft tissue and soft material have small X-ray absorption properties, so sufficient contrast for the X-ray absorption contrast image cannot be obtained. For example, articular cartilage and its surrounding synovial fluid, both constituting a human joint, are mainly made of water, so there is little difference between their amounts of X-ray absorption, resulting in poor image contrast.

Recently, X-ray phase imaging has been studied actively. The X-ray phase imaging obtains an image (hereafter referred to as phase contrast image) based on phase shift of the X-ray wave front caused by the difference in refraction index of an object, instead of intensity variations of the X-ray caused by the object. When the X-rays are traversing the object, the phase of the X-ray wave front is much affected compared with the amplitude of the X-ray. Accordingly, the X-ray phase contrast imaging based on the phase difference makes it possible to obtain a high contrast image even if the object has low X-ray absorption property.

A radiation imaging system for obtaining a phase contrast image is suggested for performing the above-described X-ray phase imaging (for example, see International Publication No. WO2008/102654, C. David, et al., "Differential X-ray Phase contrast imaging using a shearing interferometer", Applied Physics Letters, Vol. 81, No. 17, October, 2002, page 3287). In the radiation imaging system, a first grating and a second grating are arranged in parallel at a predetermined interval, and a self-image of the first grating is formed at the position of the second grating. The intensity of the self-image is modulated by the second grating to obtain the phase contrast image. The phase information of the object is reflected on a fringe image obtained by the intensity modulation of the self-image.

There are various methods to obtain phase information of the object using the above-described fringe image. Fringe scanning method, Moiré interference measurement method, and Fourier transform method are known. For example, in International Publication No. WO2008/102654, the fringe scanning method is used. The fringe scanning method is a method in which image capture is performed after each translational movement while one of first and second gratings is translationally moved relative to the other by a predetermined amount smaller than a grating pitch in a direction approximately orthogonal to a grating line to obtain fringe images and then a phase differential value corresponding to an amount of X-ray phase variation is obtained based on intensity variations in each pixel data. A phase contrast image is generated based on the phase differential value. The fringe scanning is applied not only to the X-ray, but also to an imaging apparatus using laser (see Hector Canabal, et al., "Improved phase-shifting method for automatic processing of moiré deflectograms" Applied Optics, Vol. 37, No. 26, September 1998, page 6227).

In the moiré interference measurement method, moiré fringes caused by a minute difference between a self-image of a first grating and a second grating are detected to obtain an amount of the X-ray phase shift based on distortion in the shape of the moiré fringes. There is no need to translationally move the grating as in the fringe scanning method. The Fourier transform method, as with the moiré interference measurement method, eliminates the need for the translational movement of the grating. The Fourier transform method is to obtain a phase differential image by obtaining spatial frequency spectrum through Fourier transform of the above-described moiré fringes and then separating spectrum corresponding to carrier frequency from the spatial frequency spectrum to perform inverse transformation.

Because the radiation imaging system disclosed in International Publication No. WO2008/102654 uses Talbot effect, a distance between the first grating and the second grating needs to be set at a value equal to Talbot length. Thus, there is a disadvantage that a grating arrangement is restricted. To solve this problem, it is known to set a distance between the first and second gratings without reference to the Talbot length by reducing X-ray diffraction at the first grating not to generate the Talbot interference so as to form a projection image of the X-ray passing through the first grating (see Chinese Patent Publication No. 101532969).

The radiation imaging system of Chinese Patent Publication No. 101532969 discloses fringe scanning method and moiré interference measurement method as methods for obtaining phase information of an object using fringe images. For the moiré interference measurement method, to surely detect the moiré fringes with an image detector, it is necessary to make the moiré fringes determined by the grating pitches of the first and second gratings larger than the pixel size of the image detector.

International Publication No. WO2008/102654 and Chinese Patent Publication No. 101532969, however, do not disclose conditions to obtain the intensity variations from each pixel in the fringe scanning method. In the fringe scanning method, imaging is performed based on a phase difference of intensity variations in each pixel between the case where an object is present and the case where an object is absent. Therefore, it is necessary to surely obtain the intensity variations from each pixel. If the intensity variations are not obtained sufficiently, accuracy of the phase differential image is degraded. As a result, a good phase contrast image cannot be obtained.

In view of the foregoing, an object of the present invention is to provide a radiation imaging system capable of surely obtaining intensity variations from each pixel and consistently obtaining a good phase contrast image.

DISCLOSURE OF INVENTION

In order to achieve the above objects and other objects, a radiation imaging system of the present invention includes a first grating, a second grating, a scanning section, a radiation image detector, and a processing section. The first grating has two or more radiation shield members extending in a first direction and arranged in a second direction at a first pitch. The second direction is orthogonal to the first direction. Radiation emitted from a radiation source passes through the first grating to generate a first periodic pattern image. The second grating has two or more radiation shield members extending in a first direction and arranged in a second direction at a second pitch. The radiation shield members of the second grating partly shield the first periodic pattern image to generate a second periodic pattern image. The scanning section moves at least one of the first grating and the second grating relative to the other in the second direction at a predetermined pitch. The radiation image detector detects the second periodic pattern image as an image signal. The processing section images phase information based on the image signal obtained by the radiation image detector. A mathematical expression $D_X \neq n \times (p_1' \times p_2')/|p_1'-p_2'|$ is satisfied where $p_1'$ denotes a period of the first periodic pattern image, relative to the second direction, at a position of the second grating, $p_2'$ denotes a substantial grating pitch of the second grating relative to the second direction, $D_X$ denotes a dimension of a radiation imaging area, relative to the second direction, of each pixel in the radiation image detector, and n denotes a positive integer.

It is preferable that a mathematical expression $D_X < (p_1' \times p_2')/|p_1'-p_2'|$ is satisfied.

It is preferable that the first grating is an absorption grating, and the radiation passed through the first grating forms the first periodic pattern image as a project image without causing Talbot interference.

It is preferable that a mathematical expression $L_2 < \{(L_1+L_2)/L_1\} \times p_1^2/\lambda$ is satisfied where $L_1$ denotes a distance between a focal point of the radiation source and the first grating, $L_2$ denotes a distance between the first grating and the second grating, $p_1$ denotes the first pitch, and $\lambda$ denotes a peak wavelength the radiation.

It is preferable that a mathematical expression $p_2 = \{(L_1+L_2)/L_1\} \times p_1$ is satisfied where $L_1$ denotes a distance between a focal point of the radiation source and the first grating, $L_2$ denotes a distance between the first grating and the second grating, $p_1$ denotes the first pitch, and $p_2$ denotes the second pitch.

It is preferable that a mathematical expression $d_2 = \{(L_1+L_2)/L_1\} \times d_1$ is satisfied where $L_1$ denotes a distance between a focal point of the radiation source and the first grating, $L_2$ denotes a distance between the first grating and the second grating, $d_1$ denotes an opening width of a slit of the first grating in the second direction, and $d_2$ denotes an opening width of a slit of the second grating in the second direction.

It is preferable that a mathematical expression $h_1 \leq \{L/(V/2)\} \times d_1$ is satisfied where L denotes a distance between a focal point of the radiation source and the radiation image detector, $h_1$ denotes thickness of the radiation shield member, of the first grating, in a direction orthogonal to the first and second directions, and V denotes a length of an effective field of view in the second direction at a detection surface of the radiation image detector.

It is preferable that a mathematical expression $h_2 \leq \{L/(V/2)\} \times d_2$ is satisfied where $h_2$ denotes thickness of the radiation shield member of the second grating in a direction orthogonal to the first and second directions.

It is preferable that the radiation imaging system further includes a radiation source having a third grating for shielding the radiation in an area-selective manner to generate a plurality of point light sources. A position of the third grating is regarded as a position of the focal point.

It is preferable that the radiation image detector is a flat panel detector in which pixels are arranged in two dimensions along the first and second directions.

The radiation imaging system further includes a changing section for changing at least one of the period $p_1'$ and the pitch $p_2'$.

It is preferable that the changing section rotates at least one of the first grating and the second grating about a rotation axis parallel to a direction orthogonal to the first and second directions.

It is preferable that the changing section inclines at least one of the first grating and the second grating about a rotation axis parallel to the first direction.

It is preferable that the changing section moves at least one of the first grating and the second grating in a direction orthogonal to the first and second directions.

It is preferable that the phase information is a phase differential image generated by calculating a phase shift value of an intensity modulated signal, and the intensity modulated signal is obtained in each pixel.

It is preferable that the processing section integrates the phase differential image in the second direction to generate a phase contrast image.

The radiation imaging system further includes a grating rotation section for rotating the first grating and the second grating at a predetermined angle about a rotation axis parallel to a direction orthogonal to the first and the second directions. The phase information is imaged before and after the rotation.

It is preferable that the radiation source and the radiation image detector are horizontally opposed to allow imaging of an object in a standing position.

It is preferable that the radiation source and the radiation image detector are opposed in the up-and-down direction to allow imaging of an object in a lying position.

It is preferable that a rotary arm holds the radiation source and the radiation image detector to allow imaging of a patient in a standing position and a lying position.

It is preferable that the radiation imaging system is a mammography apparatus allowing imaging of a breast as an object.

It is preferable that the radiation imaging system further includes an interlocking movement section for moving the radiation source, the first grating, the intensity modulator and the radiation image detector in an interlocking manner in an optical axis direction relative to an object and a controller for controlling the interlocking movement section according to a magnification to adjust a distance between the radiation source and the object.

It is preferable that the radiation imaging system further includes an image detector moving section for moving the radiation image detector relative to the object in an optical axis direction and a controller for controlling the image detector moving section according to a magnification to adjust a distance between the radiation source and the radiation image detector.

It is preferable that the first grating and the second grating are arranged along a cylindrical surface having a line passing through a focal point of the radiation source as an axis.

It is preferable that the first grating and the second grating extend along a direction of a curve of the cylindrical surface.

It is preferable that the radiation imaging system further includes a rotational movement section for integrally moving the radiation source, the first grating, the second grating, and the radiation image detector about an object, and a three dimensional image producing section for producing a three dimensional image based on two or more pieces of phase information obtained at different rotation angles rotated by the rotational movement section.

It is preferable that the radiation imaging system further including a position changing section for changing a relative position between the radiation image detector and the radiation source in the first direction, and a stereo image producing section for producing a stereo image based on the phase information obtained at first and second relative positions changed by the position changing section.

It is preferable that the radiation imaging system further includes an absorption contrast image generating section for obtaining a value related to an average value of pixel data for each pixel in the radiation image detector to generate an absorption contrast image.

It is preferable that the radiation imaging system further includes a small angle scattering image generating section for obtaining a value related to variation from the average value of pixel data for each pixel in the radiation detector to generate a small angle scattering image.

A radiation imaging system of the present invention includes a first grating, an intensity modulator, a radiation image detector, and a processing section. The first grating has two or more radiation shield members extending in a first direction and arranged in a second direction at a first pitch. The second direction is orthogonal to the first direction. Radiation emitted from a radiation source passes through the first grating to generate a first periodic pattern image. The intensity modulator varies intensity of the first periodic pattern image at least at one relative position having a phase different from a phase of the first periodic pattern in the second direction. The radiation image detector detects a second periodic pattern image as an image signal. The second periodic pattern image is generated by the intensity modulator at each of the relative positions. The processing section images phase information based on the image signal obtained by the radiation image detector. A mathematical expression $h_1 \leq \{L/(V/2)\} \times d_1$ is satisfied where L denotes a distance between a focal point of the radiation source and the radiation image detector, $h_1$ denotes thickness of the radiation shield member of the first grating in a direction orthogonal to the first and second directions, $d_1$ denotes an opening width of a slit of the first grating in the second direction, and V denotes a length of an effective field of view in the second direction at a detection surface of the radiation image detector.

It is preferable that the intensity modulator is composed of a second grating having two or more radiation shield members extending in the first direction and arranged at a second pitch in the second direction. The radiation shield members partly shield the first periodic pattern image to generate a second periodic pattern image. A mathematical expression $h_1 \leq \{L/(V/2)\} \times d_2$ is satisfied where $h_2$ denotes thickness of the radiation shield member of the second grating in a direction orthogonal to the first and second directions, $d_2$ denotes an opening width of a slit of the second grating in the second direction.

According to the present invention, a mathematical expression $D_X \neq n \times (p_1' \times p_2')/|p_1' - p_2'|$ is satisfied where $p_1'$ denotes a period of the first periodic pattern image, relative to the second direction, at a position of the second grating, $p_2'$ denotes a substantial grating pitch of the second grating relative to the second direction, and $D_X$ denotes a dimension of a radiation imaging area, relative to the second direction, of each pixel in the radiation image detector. Thereby, the intensity variations changes are surely obtained from each pixel, and good phase contrast image is obtained consistently.

BEST MODE FOR CARRYING OUT THE INVENTION

First Embodiment

Figure 1:
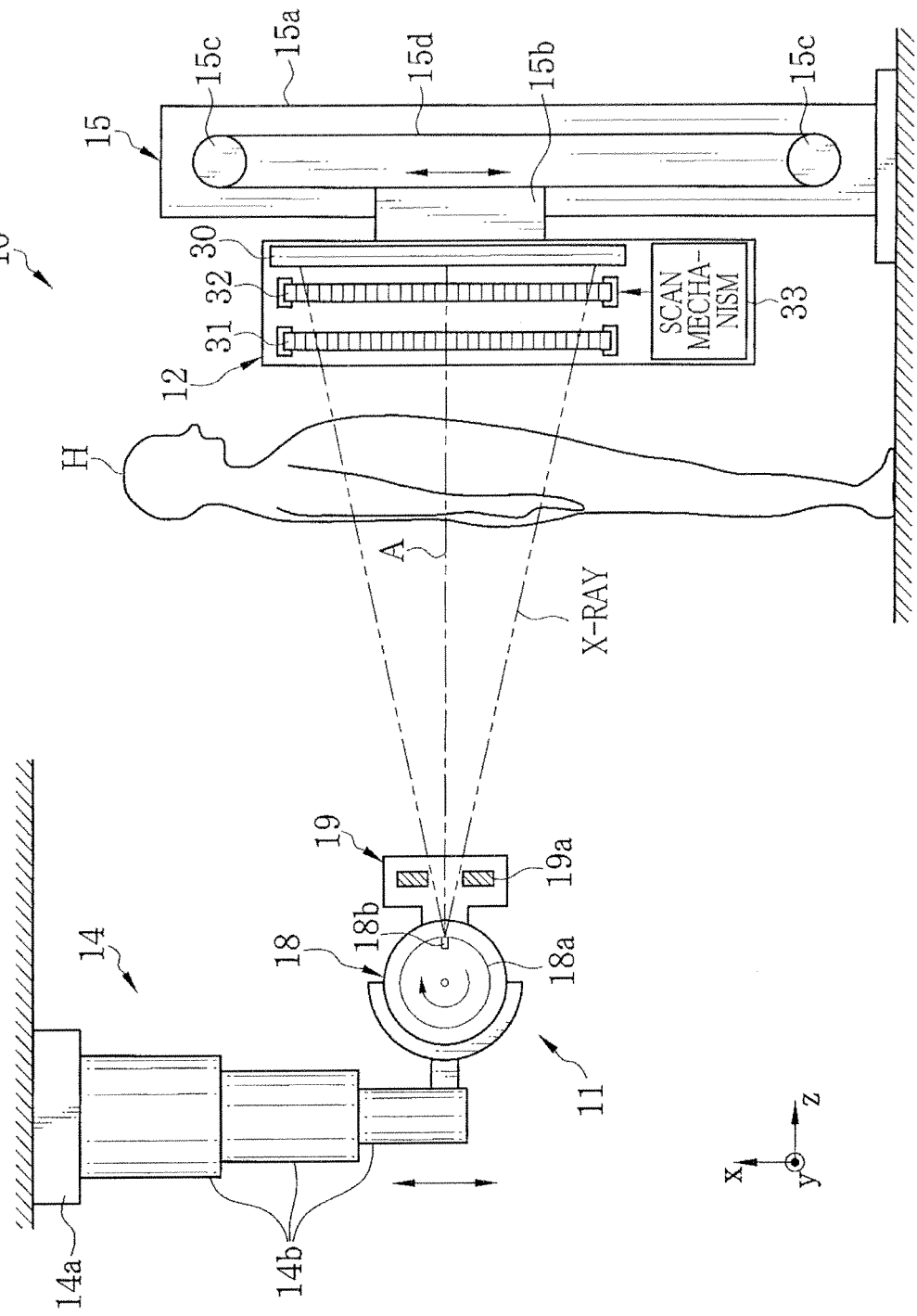
FIG. 1 is a schematic diagram of an X-ray imaging system according to a first embodiment of the present invention.
Figure 2:
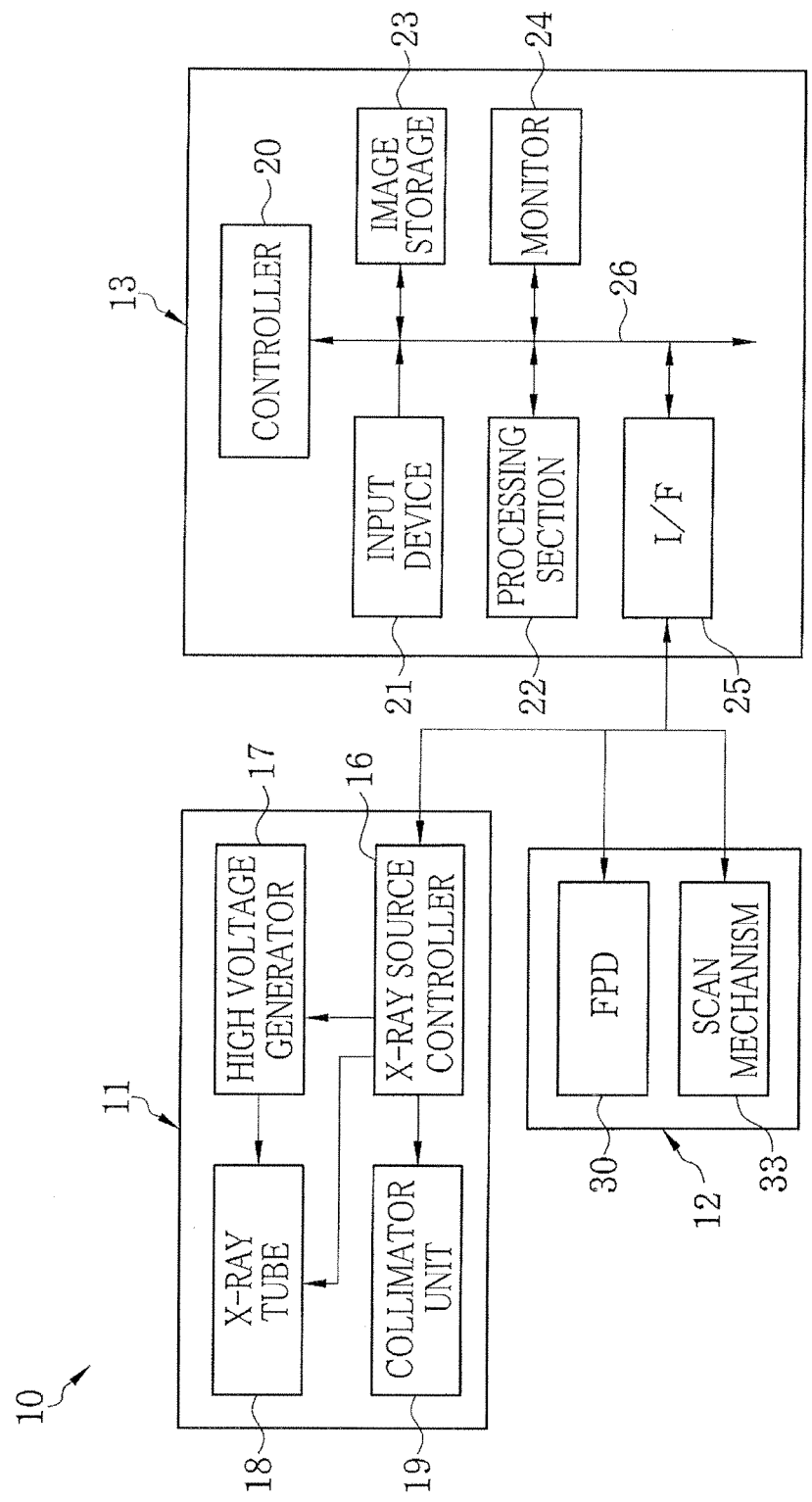
FIG. 2 is a block diagram of a control configuration of the X-ray imaging system according to the first embodiment of the present invention.

In FIGS. 1 and 2, an X-ray imaging system 10 according to a first embodiment of the present invention is an X-ray diagnostic apparatus for capturing an image of an object (patient) H in a standing position. The X-ray imaging system 10 is composed of an X-ray source 11, an imaging unit 12, and a console 13. The X-ray source 11 irradiates the object H with X-ray. The imaging unit 12 is opposed to the X-ray source 11, and detects the X-ray passed through the object H to generate image data. The console 13 controls the exposure of the X-ray source 11 and the image capture of the imaging unit 12 based on operation of an operator. The console 13 also processes image data, obtained by the imaging unit 12, to generate a phase contrast image.

An X-ray source holder 14 holds the X-ray source 11 such that the X-ray source 11 is movable in a vertical or up-and-down direction (x direction). The X-ray source holder 14 is suspended from a ceiling. An upright stand 15, placed on a floor, movably holds the imaging unit 12 in the vertical or up-and-down direction (x direction).

The X-ray source 11 is composed of an X-ray tube 18 and a collimator unit 19. The X-ray tube 18 generates X-ray in accordance with high voltage applied from a high voltage generator 17 under the control of an X-ray source controller 16. The collimator unit 19 is provided with a movable collimator 19a. The collimator 19a restricts X-ray irradiation field of the X-ray from the X-ray tube 18 to shield an area of the object H other than the area under inspection from the X-ray. The X-ray tube 18 is a rotating anode type. The X-ray tube 18 includes a filament (not shown) as a cathode that emits electrons towards the rotating anode. The emitted electron beams impinge on a rotating anode 18a rotating at a predetermined speed to generate the X-ray. An X-ray focal point 18b is an area of the rotating anode 18a on which the electron beams impinge.

The X-ray source holder 14 is composed of a movable carriage 14a and column sections 14b. The carriage 14a is movable along a ceiling rail (not shown) provided on the ceiling in a horizontal direction (z direction). The column sections 14b are coupled to each other in the up-and-down direction. The carriage 14a is provided with a motor (not shown) for extending or contracting the column sections 14b to change a position of the X-ray source 11 in the up-and-down direction.

The upright stand 15 is composed of a body 15a and the holding section 15b. The body 15a is placed on the floor. The holding section 15b for holding the imaging unit 12 is attached to the body 15a such that the holding section 15b is movable in the up-and-down direction. The holding section 15b is connected to an endless belt 15d. The endless belt 15d is looped over pulleys 15c placed apart from each other in the up-and-down direction. The holding section 15b is driven or moved with a motor (not shown) for rotating the pulleys 15c. A controller 20 provided in the console 13 drives the motor based on the setting operation of the operator.

The upright stand 15 is provided with a position sensor (not shown) such as a potentiometer. The position sensor measures an amount of movement of the pulley 15c or the endless belt 15d to detect a position of the imaging unit 12 in the up-and-down direction. A value detected by the position sensor is provided to the X-ray source holder 14 via a cable. The X-ray source holder 14 extends or contracts the column sections 14b based on the detected value to move the X-ray source 11 to follow the up or down movement of the imaging unit 12.

The console 13 is provided with the controller 20 composed of a CPU, a ROM, a RAM, and the like. In addition to the controller 20, the console 13 is provided with an input device 21, a processing section 22, an image storage 23, a monitor 24, and an interface (I/F) 25. Through the input device 21, the operator inputs an instruction for imaging and its details. The processing section 22 processes image data obtained with the imaging unit 12 to generate a phase contrast image. The image storage 23 stores the phase contrast image. The monitor 24 displays the phase contrast image. The I/F 25 is connected to each section of the X-ray imaging system 10. The input device 21, the processing section 22, the image storage 23, the monitor 24, and an interface (I/F) 25 are connected to the controller 20 through a bus 26.

For example, a switch, a touch panel, a mouse, or a key board can be used as the input device 21. Through the operation of the input device 21, X-ray imaging conditions such as X-ray tube voltage and X-ray exposure time, and image capture timing are input. The monitor 24 is composed of a liquid crystal display or the like. Under the control of the controller 20, the monitor 24 displays text information such as X-ray imaging condition and the phase contrast image.

The imaging unit 12 is provided with a flat panel detector (FPD) 30, a first absorption grating 31, and the second absorption grating 32. The FPD 30 is composed of a semiconductor circuit. The first and second absorption gratings 31 and 32 are used for performing phase imaging in which phase variations (angular variations) of X-ray caused by the object H are detected. The FPD 30 is placed such that its detection surface is orthogonal to an optical axis A of the X-ray from the X-ray source 11. The first and second absorption gratings 31 and 32 are arranged between the FPD 30 and the X-ray source 11. In addition, the imaging unit 12 is provided with a scan mechanism 33. The scan mechanism 33 moves the second absorption grating 32 in the up-and-down direction translationally relative to the first absorption grating 31 to change the position of the second absorption grating 32 relative to the first absorption grating 31. The scan mechanism 33 is composed of, for example, an actuator such as an piezoelectric element. An intensity modulator is composed of the second absorption grating 32 and the scan mechanism 33.

Figure 3:
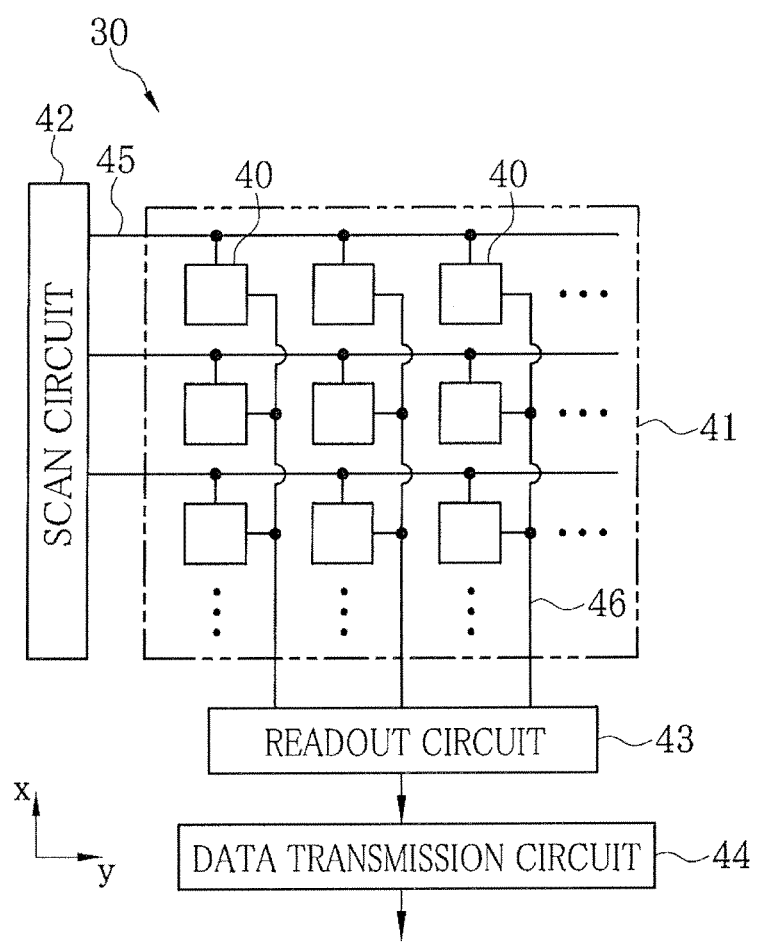
FIG. 3 is a schematic diagram of a flat panel detector.

In FIG. 3, the FPD 30 is composed of an imaging section 41, a scan circuit 42, a readout circuit 43, and a data transmission circuit 44. The imaging section 41 is composed of pixels 40 arranged in two dimensions in x and y directions on an active matrix substrate. Each pixel 40 converts the X-ray into electric charge to accumulate the electric charge. The scan circuit 42 switches a row to read the electric charge from the imaging section 41. The readout circuit 43 reads the electric charge accumulated in each pixel 40 to convert the electric charge into image data, and stores the image data. The data transmission circuit 44 transmits the image data to the processing section 22 via the I/F 25 in the console 13. A scan line 45 connects the scan circuit 42 and the pixels 40 in each row. A signal line 46 connects the readout circuit 43 and the pixels 40 in each column.

Each of the pixels 40 is a direct conversion type X-ray sensing element which directly converts the X-ray into the electric charge with the use of a photo conductive layer (not shown) made from amorphous selenium and the like and then accumulates the electric charge in a capacitor (not shown) connected to electrodes below the photo conductive layer. To each pixel 40, a TFT switch (not shown) is connected. A gate electrode of the TFT switch is connected to the scan line 45. A source electrode of the TFT switch is connected to the capacitor. A drain electrode of the TFT switch is connected to the signal line 46. When a drive pulse from the scan circuit 42 turns on the TFT switch, the signal line 46 reads the electric charge accumulated in the capacitor.

Each of the pixels 40 may be an indirect conversion type X-ray sensing element which converts the X-ray into visible light with the use of a scintillator (not shown) made from gadolinium oxide ($Gd_2O_3$), cesium iodide (CsI), or the like and then converts the visible light into electric charge with the use of a photodiode (not shown) to accumulate the electric charge. In this embodiment, the FPD having a TFT panel is used as the radiation image detector. Alternatively or in addition, various radiation image detectors having a solid image sensor such as a CCD sensor or a CMOS sensor may be used.

The readout circuit 43 is composed of an integrating amplifier circuit, an A/D converter, a correction circuit, and image memory (all not shown). The integrating amplifier circuit integrates the electric charge outputted from each of the pixels 40 through the signal line 46 to convert the integrated electric charge into a voltage signal (image signal). The integrating amplifier circuit inputs the image signal to the A/D converter. The A/D converter converts the image signal into digital image data, and then inputs the digital image data to the correction circuit. The correction circuit performs offset correction, gain correction, and linearity correction to the image data. The correction circuit stores the corrected image data in the image memory. The correction processes performed by the correction circuit may include correction of X-ray exposure amount, correction of X-ray exposure distribution (so-called shading), and correction of pattern noise (for example, a leakage signal of the TFT switch) which depends on control conditions (for example, drive frequency and reading period) of the FPD 30.

Figure 4:
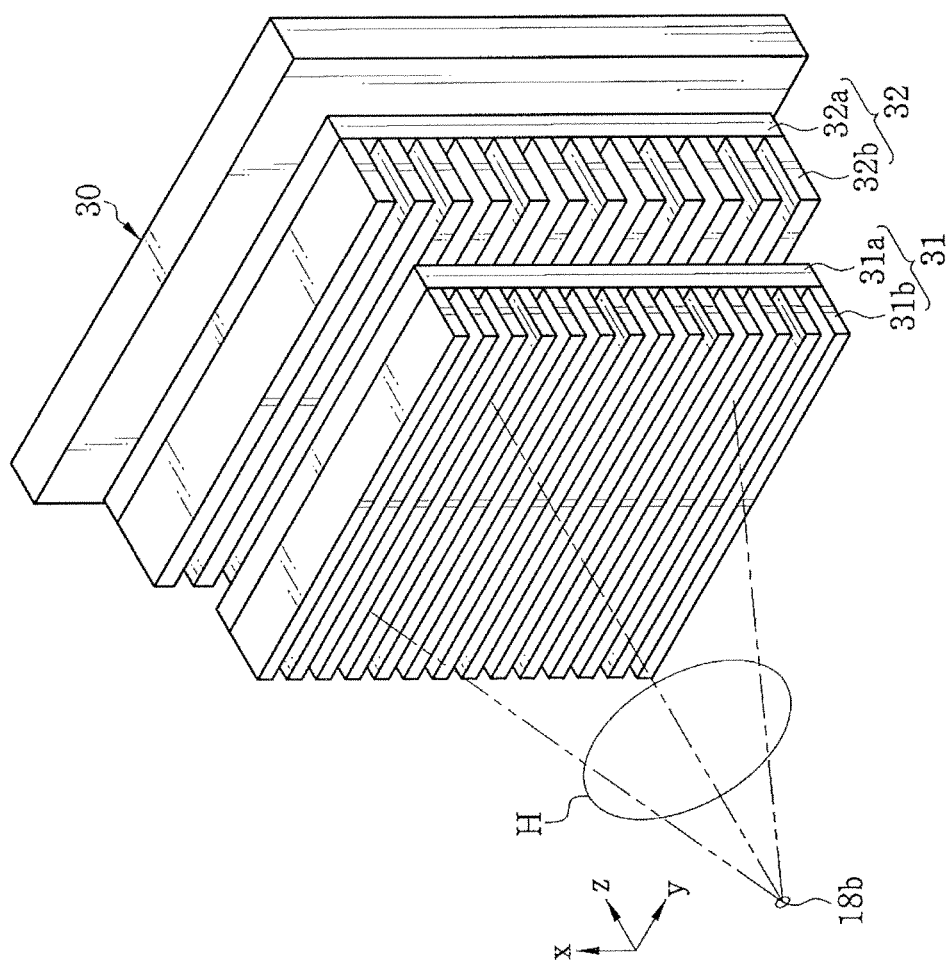
FIG. 4 is a perspective view of first and second absorption gratings.
Figure 5:
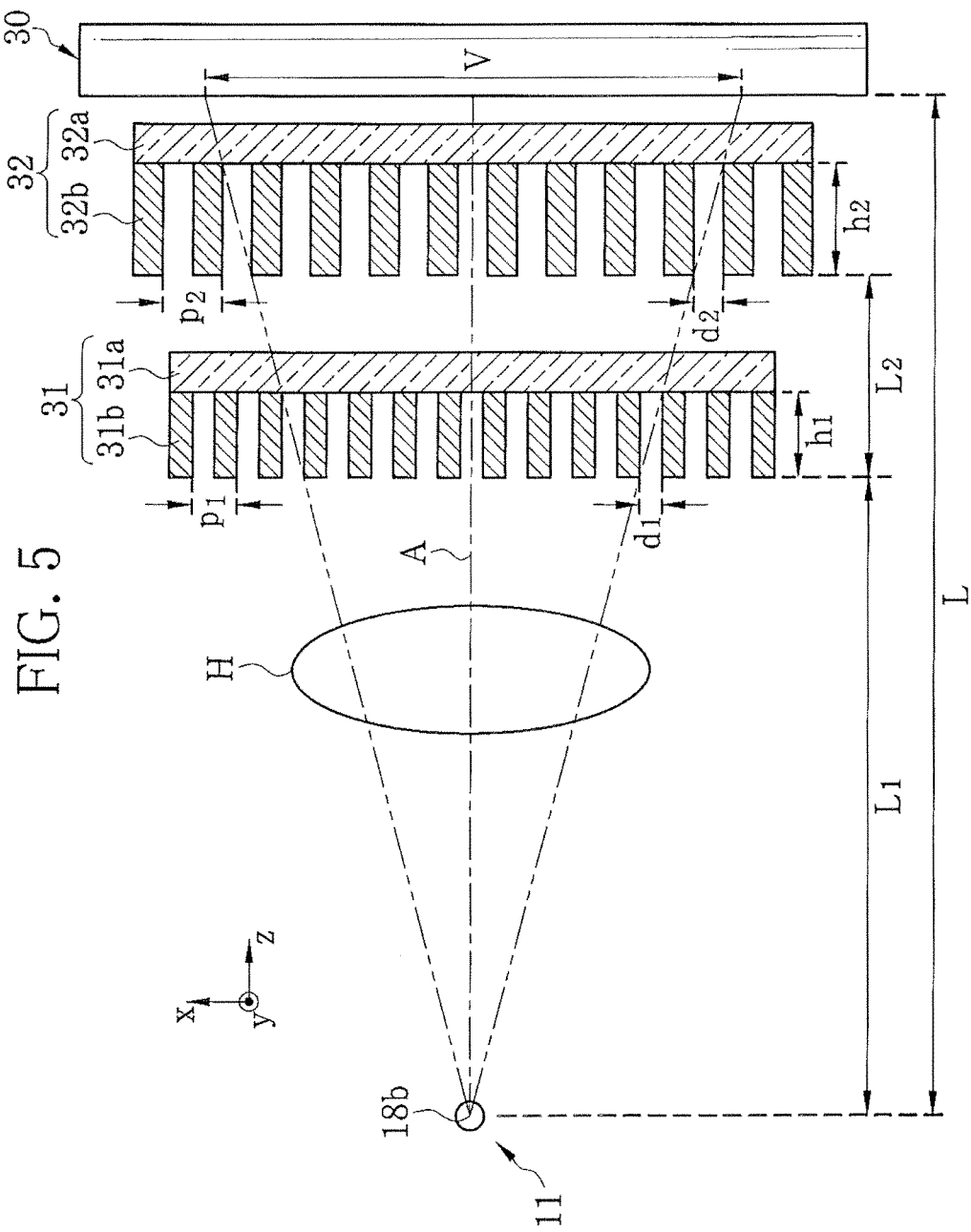
FIG. 5 is a lateral view of the first and second absorption gratings.

In FIGS. 4 and 5, the first absorption grating 31 is composed of a substrate 31a and a plurality of X-ray shield members 31b arranged on the substrate 31a. Similarly, the second absorption grating 32 is composed of a substrate 32a and a plurality of X-ray shield members 32b arranged on the substrate 32a. Each of the substrates 31a and 32a is formed of an X-ray transmission member such as glass.

Each of the X-ray shield members 31b and 32b is a linear member extended in a direction (y direction orthogonal to the x and z directions) in a plane orthogonal to the optical axis A of the X-ray from the X-ray source 11. Each of the X-ray shield members 31b and 32b is preferably formed of a material having excellent X-ray absorbing properties, for example, metal such as gold and platinum. The X-ray shield members 31b and 32b can be formed using metal plating and/or vapor deposition, for example.

The X-ray shield members 31b are arranged at regular intervals at a predetermined opening width $d_1$ and at a constant pitch $p_1$ in a direction (x direction) orthogonal to the above described y direction in a plane orthogonal to the optical axis A of the X-ray. Similarly, the X-ray shield members 32b are arranged at regular intervals at a predetermined opening width $d_2$ and at a constant pitch $p_2$ in a direction (x direction) orthogonal to the above described y direction in a plane orthogonal to the optical axis A of the X-ray. The first and second absorption gratings 31 and 32 do not modify the phase of the incident X-ray but modify the intensity of the incident X-ray, so the first and second absorption gratings 31 and 32 are also referred to as amplitude gratings. Slits between the X-ray shield members 31b (an area with the opening width $d_1$) and the slits between the X-ray shield members 32b (an area with the opening width $d_2$) may not be gaps or empty spaces. The slits may be filled with a low X-ray absorption material, for example, polymer material or light metal.

The first and second absorption gratings 31 and 32 are arranged to project the most of the X-ray fractions passed through the slits in a geometrical-optical manner under less contribution of Talbot interference. The first absorption grating 31 forms a first periodic pattern image (G1 image). The second absorption grating 32 forms a second periodic pattern image (G2 image).

To be more specific, each of the opening widths $d_1$ and $d_2$ of the first and second absorption gratings 31 and 32 is set at the dimension sufficiently larger than a peak wavelength of the X-ray from the X-ray source 11. Thereby, most of the X-ray passes through the slits in straight lines without diffraction. For example, when tungsten is used as the rotating anode 18a and the tube voltage is 50 kV, the peak wavelength of the X-ray is approximately 0.4 Å. In this case, by setting each of the opening widths $d_1$ and $d_2$ at a value approximately ranging from 1 µm to 10 µm, most of the X-ray is projected in the geometrical-optical manner without diffraction at the slits.

The X-ray source 11 emits the X-ray divergently from the X-ray focal point 18b as a light emission point, so-called "cone beam" X-ray. Thus, the G1 image formed by the first absorption grating 31 is enlarged in proportion to a distance from the X-ray focal point 18b. The grating pitch $p_2$ and the opening width $d_2$ of the second absorption grating 32 are determined such that the slits of the second absorption grating 32 approximately coincide with the periodic pattern of the bright areas of the G1 image at the position of the second absorption grating 32. When $L_1$ denotes a distance between the X-ray focal point 18b and the first absorption grating 31 and $L_2$ denotes a distance between the first absorption grating 31 and the second absorption grating 32, the grating pitch $p_2$ and the opening width $d_2$ are determined to satisfy the following mathematical expressions (1) and (2).

$$p_2 = \frac{L_1 + L_2}{L_1} p_1 \quad (1)$$

$$d_2 = \frac{L_1 + L_2}{L_1} d_1 \quad (2)$$

In the Talbot interferometer, the distance $L_2$ between the first absorption grating 31 and the second absorption grating 32 is restricted by the Talbot length that is defined by a grating pitch $p_1$ of the first diffraction grating 31 and the X-ray wavelength. In the imaging unit 12 of this embodiment, on the other hand, the first absorption grating 31 passes through the incident X-ray without diffraction to produce a projection or projected image. The G1 image of the first absorption grating 31 can be similarly obtained at any position behind the first absorption grating 31. As a result, the distance $L_2$ can be set independently of or without reference to the Talbot length.

As described above, the imaging unit 12 of this embodiment is not a Talbot interferometer. On the other hand, with the assumption that the X-ray is diffracted by the first absorption grating 31, a virtual Talbot length Z is represented by a mathematical expression (3) where "$p_1$" denotes the grating pitch of the first absorption grating 31, "$p_2$" denotes the grating pitch of the second absorption grating 32, "λ" denotes the X-ray wavelength (the peak wavelength), and "m" denotes a positive integer.

$$Z = m \frac{p_1 p_2}{\lambda} \quad (3)$$

The mathematical expression (3) represents the Talbot length when the X-ray source 11 emits the X-ray in cone beams. The mathematical expression (3) is known according to "Sensitivity of X-ray phase Imaging based on Talbot Interferometry" (Atsushi Momose, et al., Japanese Journal of Applied Physics, Vol. 47, No. 10, October 2008, page 8077).

An object of this embodiment is to obtain a low-profile imaging unit 12. To achieve the object, the distance $L_2$ is set at a value smaller than a minimum Talbot length obtained when m=1. Namely, the distance $L_2$ is set at a value within a range satisfying a mathematical expression (4).

$$L_2 < \frac{p_1 p_2}{\lambda} \quad (4)$$

To generate an image of a periodic pattern with high contrast, it is preferable that the X-ray shield members 31b and 32b completely shield (absorb) the X-ray. Although the above-described materials (gold, platinum, or the like) having excellent X-ray absorbing properties may be used for producing the X-ray shield members 31b and 32b, some of the X-ray passes through the first and second absorption gratings 31 and 32 without absorption. To improve the X-ray shield performance, it is preferable to increase the thicknesses $h_1$ and $h_2$ of the X-ray shield members 31b and 32b as much as possible. For example, when the tube voltage of the X-ray tube 18 is 50 kV, it is preferable to shield at least 90% of the X-ray emitted. In this case, each of the thicknesses $h_1$ and $h_2$ is preferably at least 30 μm (Au equivalent thickness).

On the other hand, when the thicknesses $h_1$ and $h_2$ of the X-ray shield members 31b and 32b are too large, it becomes difficult for the X-ray, diagonally entering the first and second absorption gratings 31 and 32, to pass through the slits. As a result, an effective field of view in a direction (x direction), orthogonal to a direction in which the X-ray shield members 31b and 32b extend, is narrowed. To secure the field of view, it is necessary to specify upper limits of the thicknesses $h_1$ and $h_2$. To ensure a length V of the effective field of view in the x direction of the detection surface of the FPD 30, the thicknesses $h_1$ and $h_2$ need to be set to satisfy mathematical expressions (5) and (6) based on geometric relationships shown in FIG. 5. Here, "L" denotes a distance between the X-ray focal point 18b and the detection surface of the FPD 30.

$$h_1 \leq \frac{L}{V/2} d_1 \quad (5)$$

$$h_2 \leq \frac{L}{V/2} d_2 \quad (6)$$

For example, when $d_1$=2.5 μm, $d_2$=3.0 μm, and L=2 m (intended to be used for normal examination in a hospital), it is necessary that the thickness $h_1$ is equal to or less than 100 μm and the thickness $h_2$ is equal to or less than 120 μm to surely obtain the length V (10 cm) of the effective field of view in the x direction.

In the above configuration, a pattern period $p_1'$ of the G1 image at the position of the second absorption grating 32 is represented by $p_1 \times (L_1+L_2)/L_1$ based on geometric relationship, and preferably equivalent to the grating pitch $p_2$ of the second absorption grating 32. There is a slight difference between the first and second absorption gratings 31 and 32 caused by production error and arrangement error. It is difficult to completely eliminate the errors. The arrangement error is relative inclination or relative rotation of the first and second absorption gratings 31 and 32, and an error caused by a variation in a pitch in the x direction due to a variation in a distance between the first and second absorption gratings 31 and 32.

When the above-described error is caused between the first and second absorption gratings 31 and 32, a difference between the pattern period $p_1'$ of the G1 image and a substantial grating pitch $p_2'$ relative to the x direction of the second absorption grating 32 generates moiré fringes in the G2 image. A period T (hereafter referred to as moiré period T) of the moiré fringes relative to the x direction is represented by a mathematical expression (7).

$$T = \frac{p_1' \times p_2'}{|p_1' - p_2'|} \quad (7)$$

In accordance with the translational movement of the second absorption grating 32 moved by the scan mechanism 33, the moiré fringes move in the moving direction (x direction) of the second absorption grating 32. In the fringe scanning method, it is necessary that the intensity of the pixel data of each pixel 40 in the FPD 30 changes in accordance with the translational movement of the second absorption grating 32 to obtain an intensity modulated signal (a waveform signal representing intensity variations in each pixel relative to the translational movement). To obtain the intensity modulated signal, it is necessary to define a relationship between the dimension of the X-ray imaging area of each pixel 40 and the moiré period T.

Figure 6A:
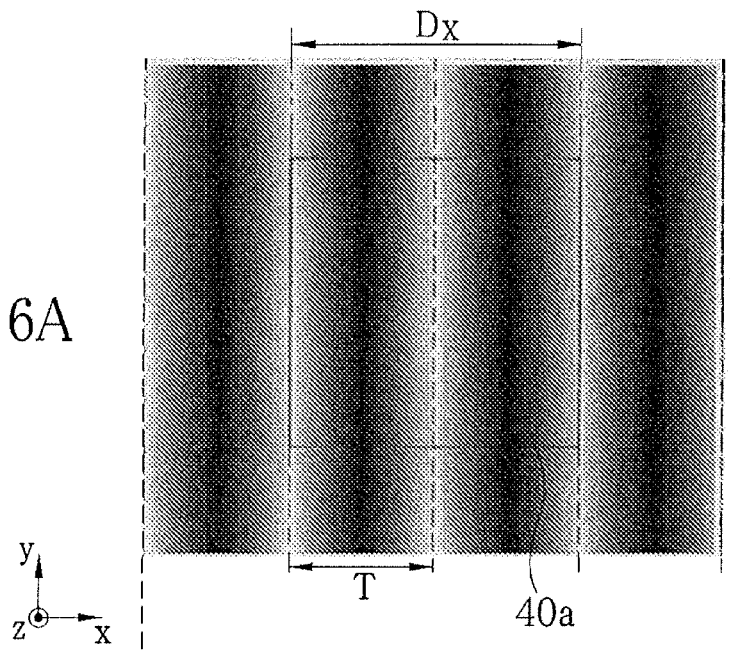
FIGS. 6A and 6B show that a dimension of an X-ray imaging area of a pixel is twice as much as the period of moiré fringes.

FIGS. 6A, 6B, 7A, and 7B show relationships between the dimension $D_X$ in the x direction of the X-ray imaging area 40a of the pixel 40 and a moiré period T. Granted that the dimension $D_X$ is equal to an integral multiple of the moiré period T as shown in FIG. 6A, although the moiré fringes move in the x direction in accordance with the fringe scanning, the same number of moiréfringes exists invariably in the X-ray imaging area 40a regardless of the positions of the moiré fringes. Accordingly, there are no changes in the intensity of the pixel data corresponding to a quantity of light received by the X-ray imaging area 40a and thus the intensity modulated signal cannot be obtained.

Figure 6B:
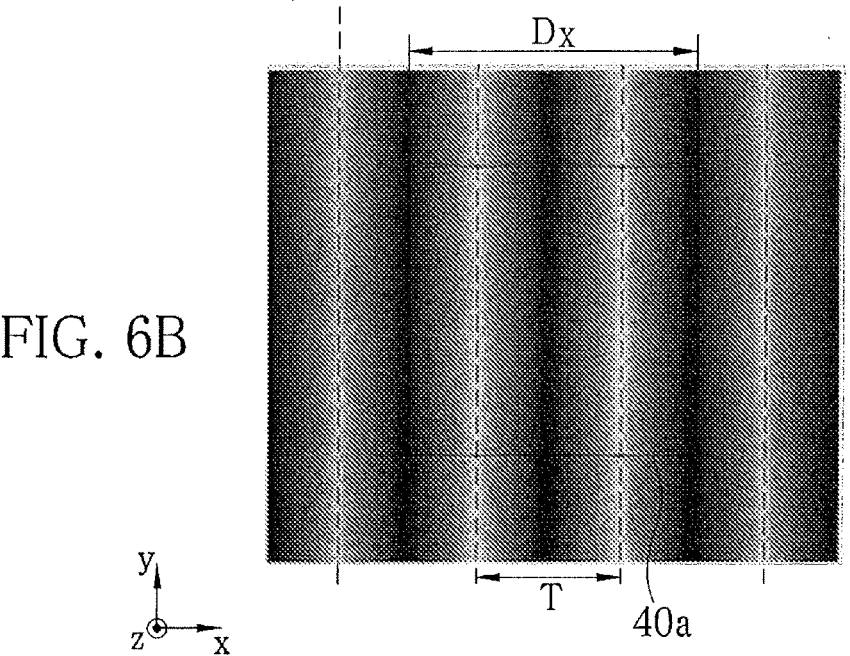
Figure 7A:
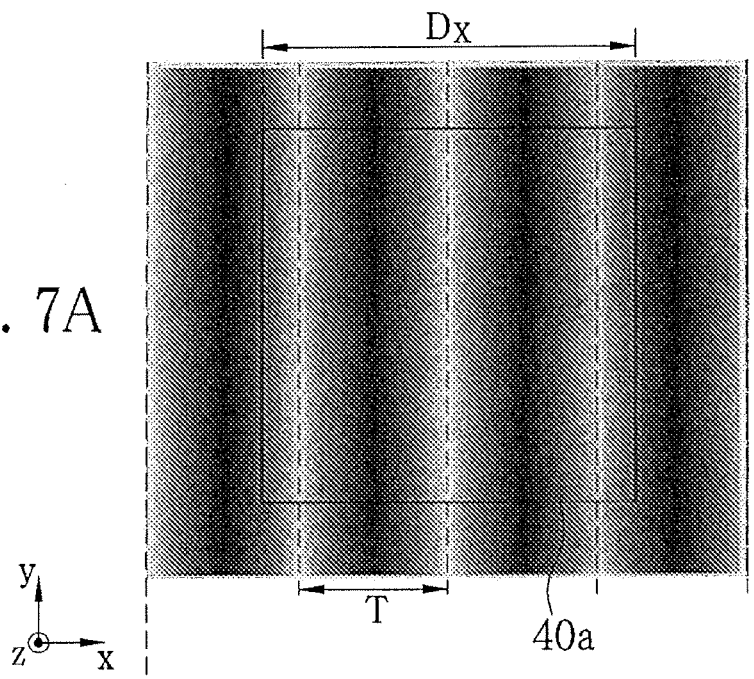
FIGS. 7A and 7B show that the dimension of the X-ray imaging area of the pixel is 2.5 times as much as the period of moiréfringes.
Figure 7B:
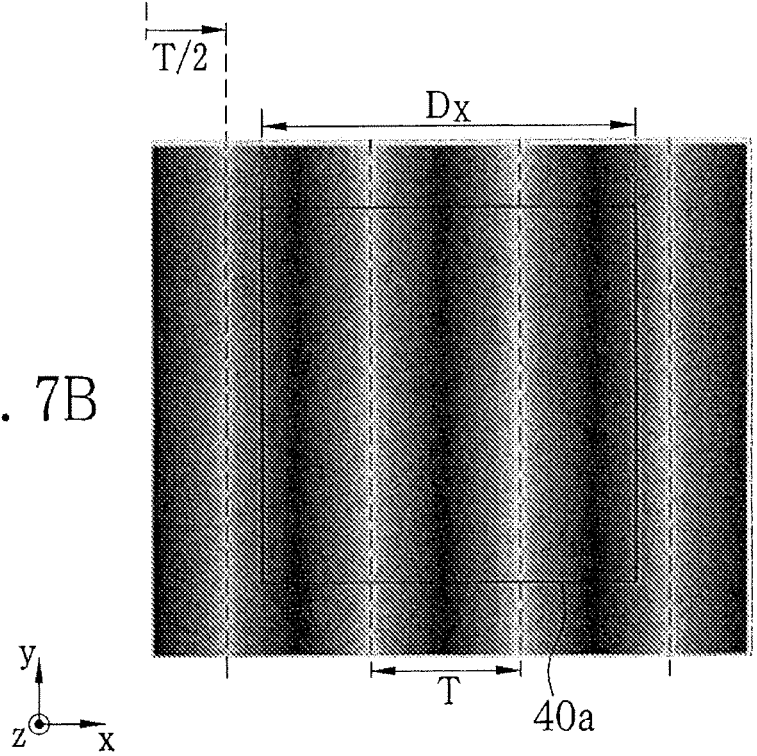

To be more specific, FIG. 6A shows that the dimension $D_X$ is twice as much as the moiré period T. In FIG. 6B, in accordance with the fringe scanning, the moiré fringes are moved from the position shown in FIG. 6A by half the moiré period T. When the fringe scanning is performed for one period, the moiré fringes return to the position shown in FIG. 6A. On the other hand, in FIG. 7A, the dimension $D_X$ is 2.5 times as much as the moiré period T. Likewise, in FIG. 7B, in accordance with the fringe scanning, the moiré fringes are moved from the position shown in FIG. 7A by half the moiré period T. When the fringe scanning is performed for one period, the moiré fringes return to the position shown in FIG. 7A.

Figure 8:
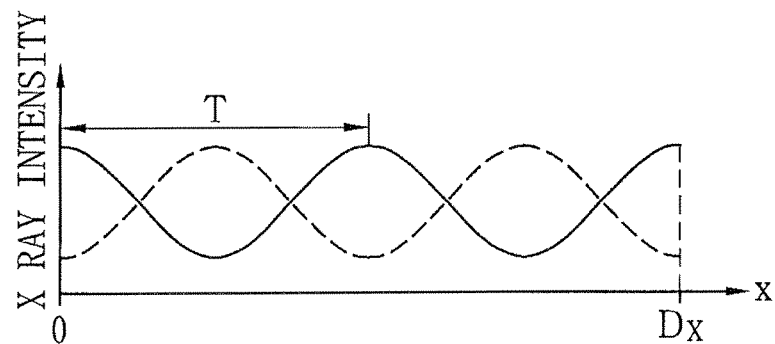
FIG. 8 is a graph showing a light quantity distribution of incident X-ray when the dimension of the X-ray imaging area of the pixel is twice as much as the period of moiré fringes.
Figure 9:
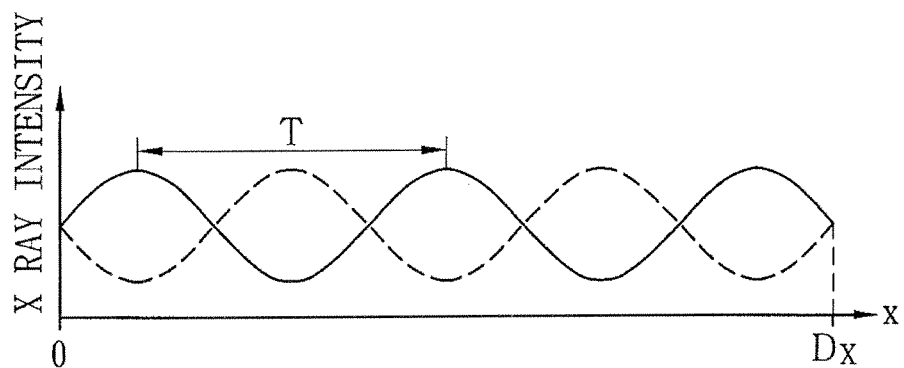
FIG. 9 is a graph showing a light quantity distribution of incident X-ray when the dimension of the X-ray imaging area of the pixel is 2.5 times as much as the period of moiré fringes.

FIGS. 8 and 9 show light quantity distribution of the X-ray incident on the X-ray imaging area 40a. In FIG. 8, a solid line shows a light quantity distribution for FIG. 6A; broken lines show a light quantity distribution for FIG. 6B. An integrated value of the light quantity distribution corresponds to the light quantity received by the X-ray imaging area 40a. As can be seen, when the dimension D is equal to an integral multiple of the moiréperiod T, the quantity of received light is constant even if the fringe scanning is performed. Accordingly, there are no intensity changes in the pixel data, so the intensity modulated signal cannot be obtained. On the other hand, in FIG. 9, a solid line shows a light quantity distribution for FIG. 7A; broken lines show a light quantity distribution for FIG. 7B. In this case, an integrated value of the light quantity distribution illustrated by the solid line differs from an integrated value of the light quantity distribution illustrated by the broken lines. Namely, in the case where the dimension $D_X$ is not an integral multiple of the moiré period T, the fringe scanning varies the quantity of received light, and thereby varies the intensity of the pixel data. Thus, the intensity modulated signal is obtained.

Accordingly, to obtain the intensity modulated signal, at least a mathematical expression (8) needs to be satisfied. To obtain an intensity modulated signal with a large amplitude, it is preferable to satisfy a mathematical expression (9) (here, "n" is a positive integer).

$$D_X \neq nT \qquad (8)$$

$$D_X < T \qquad (9)$$

Figure 10:
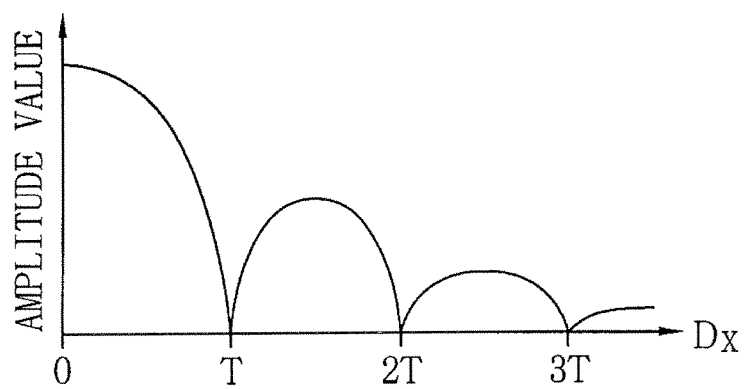
FIG. 10 is a graph showing a relationship between the dimension of the X-ray imaging area and an amplitude value of an intensity modulated signal.

FIG. 10 shows a relationship between an amplitude value of an intensity modulated signal and the dimension $D_X$ of the X-ray imaging area 40a. To obtain a large amplitude value, it is preferable that the dimension $D_X$ satisfies the mathematical expression (9) and that the dimension $D_X$ be as small as possible. As can be seen, even if $D_X > T$, a large amplitude value is obtained when the dimension $D_X$ satisfies the mathematical expression (8) and the dimension $D_X$ is close to half the integral multiple of the period T.

The dimension $D_X$ of the X-ray imaging area 40a is a value (generally approximately 100 μm) determined by design and cannot be changed. To adjust the dimensional relationship of the dimension $D_X$ and the moiré period T, positions of the first and second absorption gratings 31 and 32 are adjusted. It is preferable to change the moiré period T by at least changing one of the pattern period $p_1'$ of the G1 image and the grating pitch $p_2'$.

Figure 11A:
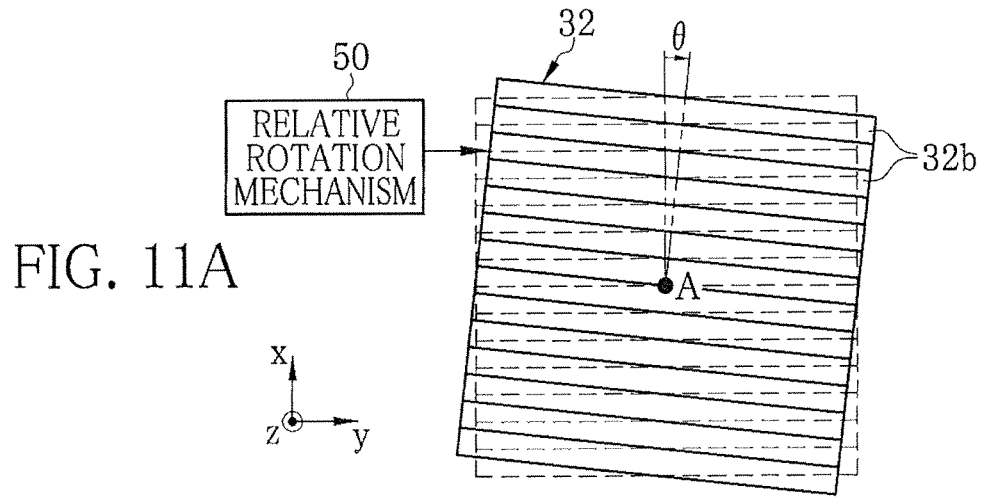
FIGS. 11A, 11B, and 11C show various mechanisms for changing a moiré period.

The moiré period T can be changed by rotating one of the first and second absorption gratings 31 and 32 relative to the other about the optical axis A. For example, as shown in FIG. 11A, a relative rotation mechanism 50 for rotating the second absorption grating 32 relative to the first absorption grating 31 about the optical axis A is provided. When the relative rotation mechanism 50 rotates the second absorption grating 32 θ degrees, the substantial grating pitch in the x direction changes from "$p_2'$" to "$p_2'/\cos\theta$". As a result, the moiré period T changes.

Figure 11B:
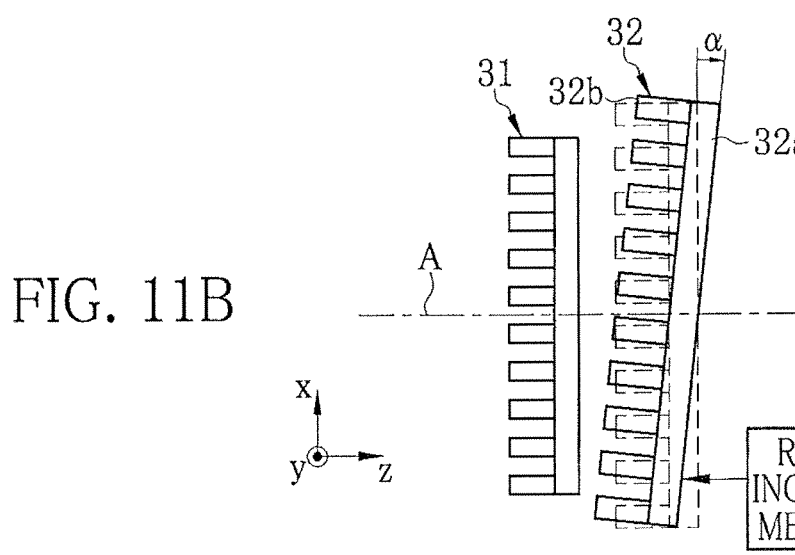

In another example, the moiré period T can be changed by inclining one of the first and second absorption gratings 31 and 32 relative to the other about an axis orthogonal to the optical axis A and extending along the y direction. For example, as shown in FIG. 11B, a relative inclination mechanism 51 for inclining the second absorption grating 32 relative to the first absorption grating 31 about an axis is provided. The axis is orthogonal to the optical axis A and extends along the y direction. When the second absorption grating 32 is inclined at an angle α by the relative inclination mechanism 51, the substantial grating pitch relative to the x direction changes from "$p_2'$" to "$p_2' \times \cos\alpha$". As a result, the moiré period T changes.

Figure 11C:
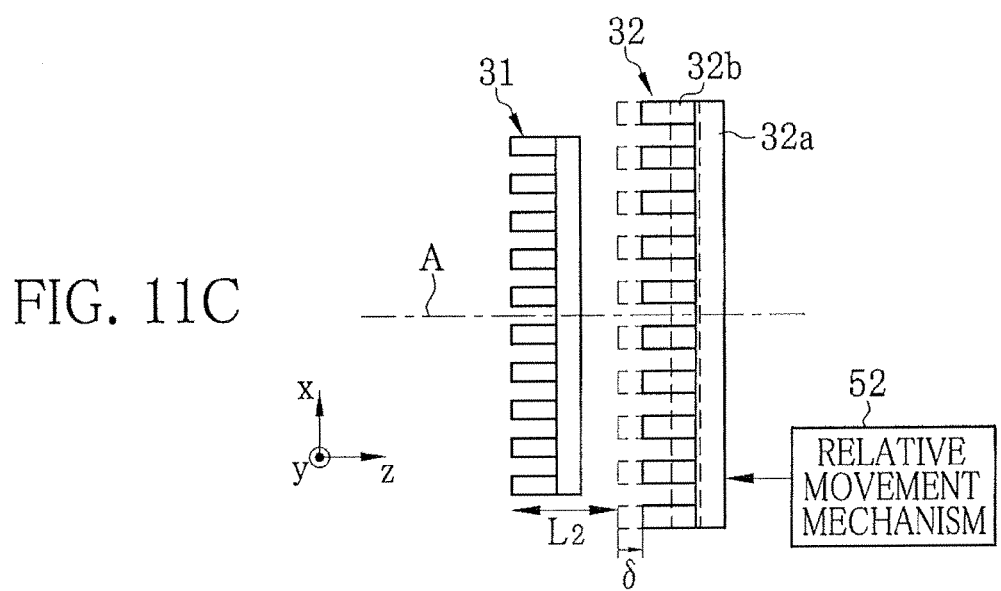

In still another example, the moiré period T can be changed by moving one of the first and the second absorption gratings 31 and 32 relative to the other in the direction of the optical axis A. For example, as shown in FIG. 11C, a relative movement mechanism 52 is provided. The relative movement mechanism 52 moves the second absorption grating 32 relative to the first absorption grating 31 in the direction of the optical axis A so as to change the distance $L_2$ between the first absorption grating 31 and the second absorption grating 32. When the relative movement mechanism 52 moves the second absorption grating 32 along the optical axis A by an amount δ, the pattern period of the G1 image of the first absorption grating 31 projected at the position of the second absorption grating 32 changes from "$p_1'$" to "$p_1' \times (L_1+L_2\delta)/(L_1+L_2)$". As a result, the moiré period T changes. In this embodiment, as described above, the imaging unit 12 does not depend on the Talbot length; the distance $L_2$ can be set without restraint. Accordingly, the relative movement mechanism 52 for changing the distance $L_2$ can be adopted.

Each of the above mechanisms (the relative rotation mechanism 50, the relative inclination mechanism 51, and the relative movement mechanism 52) for relatively moving the first or second absorption grating 31 or 32 to change the moiré period T can be composed of an actuator such as a piezoelectric element.

When the object H is arranged between the X-ray source 11 and the first absorption grating 31, the object H shifts the phase of the intensity modulated signal obtained by the fringe scanning. The phase shift value is in proportional to an angle of the X-ray deflected by the refraction effect of the object H. Accordingly, by obtaining a phase shift value of the intensity modulated signal, a phase contrast image of the object H is generated.

Figure 12:
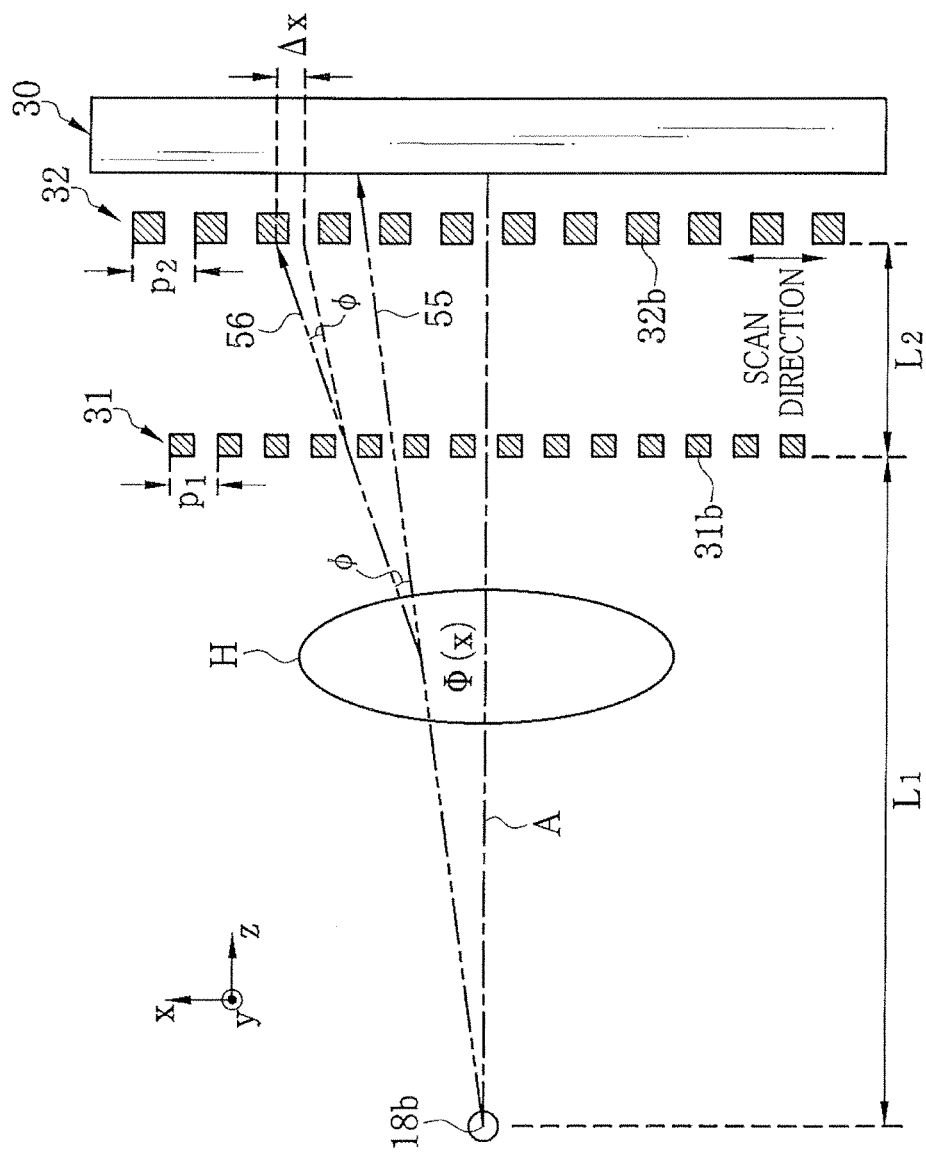
FIG. 12 is an explanatory view for describing refraction of X-ray caused by an object.

FIG. 12 shows an X-ray path refracted in accordance with the phase shift distribution Φ (x) relative to the X direction of the object H. A numeral 55 shows an X-ray path of the X-ray traveling in straight lines where the object H is absent. The X-ray traveling along the X-ray path 55 passes through the first and second absorption gratings 31 and 32 and then enters the FPD 30. A numeral 56 shows an X-ray path refracted by the object H where the object H is present. The X-ray traveling along the X-ray path 56 passes through the first absorption grating 31, and then is shielded by the second absorption grating 32.

The phase shift distribution Φ (x) of the object H is represented by a mathematical expression (10) where "n(x, z)" denotes refractive index distribution of the object H; "z" denotes an X-ray traveling direction. Here, for the sake of simplicity, the y coordinate is omitted.

$$\Phi(x) = \frac{2\pi}{\lambda} \int [1 - n(x, z)] dz \qquad (10)$$

The G1 image formed at the position of the second absorption grating 32 is displaced in the x direction with an amount corresponding to a refraction angle ϕ of the X-ray refracted by the object H. Because the refraction angle ϕ of the X-ray is extremely small, a displacement Δx is approximately expressed by a mathematical expression (11).

$$\Delta x \sim L_2 \phi \qquad (11)$$

Here, the refraction angle ϕ is represented by a mathematical expression (12) using an X-ray wavelength λ and the phase shift distribution Φ (x) of the object H.

$$\varphi = \frac{\lambda}{2\pi} \frac{\partial \Phi(x)}{\partial x} \qquad (12)$$

Thus, the displacement Δx of the G1 image, caused by the X-ray refracted by the object H, relates to the phase shift distribution Φ (x) of the object H. A mathematical expression (13) represents a relationship between the displacement Δx and a phase shift value ψ of the intensity modulated signal obtained from each pixel 40 of the FPD 30. The phase shift value ψ is a value of the phase shift of the intensity modulated signal of each pixel 40 between where the object H is present and where the object H is absent.

$$\psi = \frac{2\pi}{p_2} \Delta x = \frac{2\pi}{p_2} L_2 \varphi \qquad (13)$$

Accordingly, obtaining the phase shift value ψ of the intensity modulated signal of each pixel 40 provides the refraction angle ϕ using the mathematical expression (13) Using the mathematical expression (12), a differential value of the phase shift distribution Φ (x) is obtained. The differential values are integrated over the x direction so that the phase shift distribution Φ (x) of the object H, that is, the phase contrast image of the object H is produced. In this embodiment, the above-described phase shift value ψ is calculated using a fringe-scanning method described below.

In the fringe-scanning method, imaging is performed while one of the first and second absorption gratings 31 and 32 is translationally moved relative to the other in the x direction. (Namely, the imaging is performed every time the phase between the grating periods of the first and second absorption gratings 31 and 32 is changed.) In this embodiment, the scan mechanism 33 moves the second absorption grating 32. The moiré fringes of the G2 image move in accordance with the movement of the second absorption grating 32. When the translational distance of the second absorption grating 32 along the x direction reaches one period (the grating pitch $p_2$) of the grating period of the second absorption grating 32 (namely, when the phase shift of the moiréfringes reaches 2π), the moiré fringes return to the original position. The G2 image is captured with the FPD 30 every time the second absorption grating 32 is moved translationally by the pitch which is an integral fraction of the grating pitch $p_2$. The intensity modulated signal of each pixel 40 is obtained from the captured images (fringe images) which are based on the G2 images. The processing section 22 processes the intensity modulated signal. Thereby, the phase shift value ψ of each intensity modulated signal is obtained.

Figure 13:
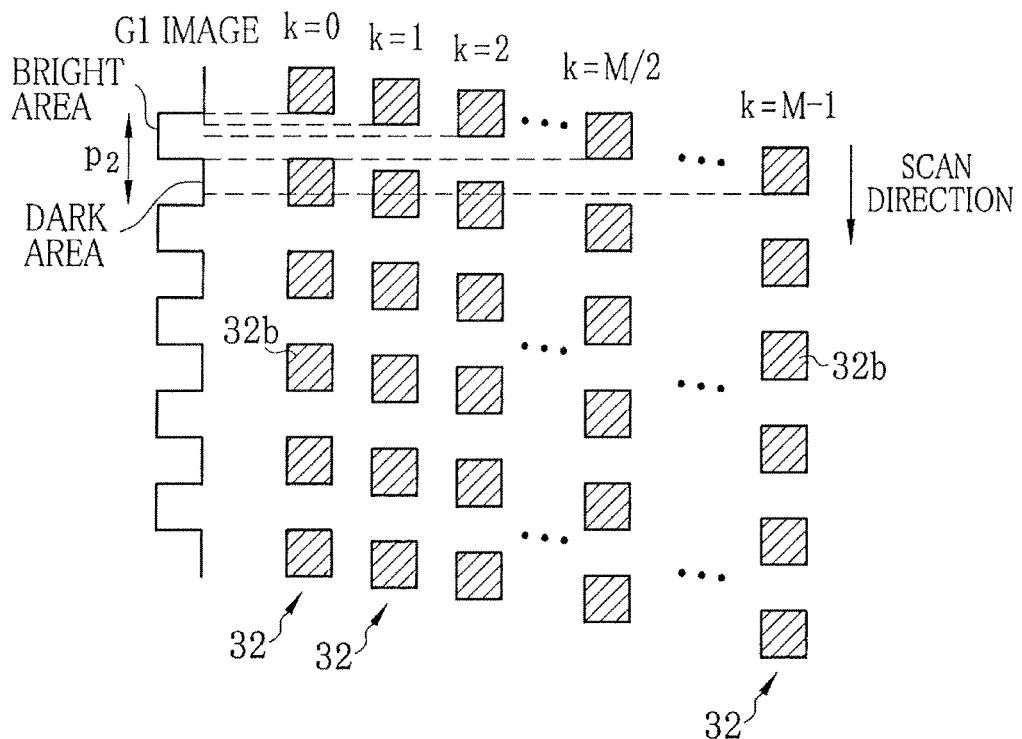
FIG. 13 is an explanatory view for describing a fringe scanning method.

FIG. 13 schematically shows that the second absorption grating 32 is moved with a scanning pitch ($p_2$/M), that is, the grating pitch $p_2$ divided by M (an integer equal to or larger than two). The scan mechanism 33 translationally moves the second absorption grating 32 to each of the M scanning positions where k=0, 1, 2, . . . , M−1 in this order. In FIG. 13, an initial position of the second absorption grating 32 is a position (k=0) where the dark areas of the G1 image approximately coincide with the X-ray shield members 32b at the position of the second absorption grating 32 in a state that the object H is absent. The initial position may be any position where k=0, 1, 2, . . . , or M−1.

When the second absorption grating 32 is at the position where k=0, the X-ray passing though the second absorption grating 32 is mainly the X-ray not refracted by the object H. As the second absorption grating 32 is sequentially moved to positions where k=1, 2, . . . , an X-ray component not refracted by the object H decreases while an X-ray component refracted by the object H increases in the X-ray passing through the second absorption grating 32. Particularly, when the second absorption grating 32 is at the position where k=M/2, the X-ray passing through the second absorption grating 32 is mainly the X-ray refracted by the object H. When the second absorption grating 32 is past the position where k=M/2, on the contrary, the X-ray component refracted by the object H decreases while the X-ray component not refracted by the object H increases in the X-ray passing through the second absorption grating 32.

When an image is captured using the FPD 30 at each of the positions where k=0, 1, 2, . . . , and M−1, M pieces of pixel data are obtained from each pixel 40. Hereafter, a method to calculate the phase shift value ψ of the intensity modulated signal of each pixel 40 using the M pieces of pixel data is described. First, a mathematical expression (14) represents pixel data $I_k$ (x) of each pixel when the second absorption grating 32 is located at a position k.

$$I_k(x) = A_0 + \sum_{n>0} A_n \exp\left[2\pi i \frac{n}{p_2} \left\{ L_2 \varphi(x) + \frac{kp_2}{M} \right\} \right] \qquad (14)$$

Here, "x" denotes a coordinate of the pixel 40 in the x-direction. "$A_0$" denotes the intensity of the incident X-ray. "$A_n$" denotes a value that relates to an amplitude value of the intensity modulated signal. Here, "i" is an imaginary number; "n" is a positive integer. "ϕ (x)" denotes the refraction angle ϕ in the form of a function of the coordinate x of the pixel 40.

Then, using a relational expression (15), the refraction angle ϕ (x) is represented by a mathematical expression (16).

$$\sum_{k=0}^{M-1} \exp\left(-2\pi i \frac{k}{M}\right) = 0 \qquad (15)$$

-continued $$\varphi(x) = \frac{p_2}{2\pi L_2} \arg\left[\sum_{k=0}^{M-1} I_k(x) \exp\left(-2\pi i \frac{k}{M}\right)\right] \quad (16)$$

Here, "arg [ ]" denotes extraction of argument and corresponds to the phase shift value ψ of the intensity modulated signal obtained from each pixel 40. By calculating the phase shift value ψ of the intensity modulated signal using the M pieces of pixel data obtained from each pixel 40 based on the mathematical expression (16), the refraction angle φ (x) is obtained.

Figure 14:
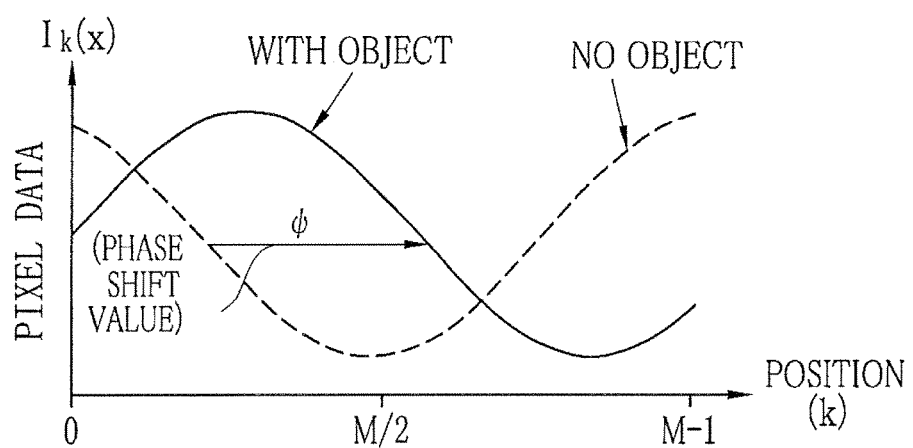
FIG. 14 is a graph showing variations in pixel data in associated with the fringe scanning.

To be more specific, as shown in FIG. 14, the values of the M pieces of pixel data obtained from each pixel 40 periodically vary relative to the position k of the second absorption grating 32 in a period of the grating pitch $p_2$. In FIG. 14, broken lines show the intensity modulated signal where the object H is absent. A solid line shows the intensity modulated signal where the object H exists. A phase difference between these two intensity modulated signals represents the phase shift value ψ.

As shown by the mathematical expression (12), the refraction angle φ (x) corresponds to a differential value of the phase shift distribution Φ (x). The phase shift distribution Φ (x) is obtained by integrating the refraction angle φ (x) along the x-axis.

In the above description, a y-coordinate in the y direction of the pixel 40 is not considered. By performing the same or similar operation to each y-coordinate, the two dimensional distribution of the refraction angle φ (x, y) is obtained. By integrating the obtained value along the x axis, the two dimensional phase shift distribution φ (x, y) is obtained. The above described operation is performed by the processing section 22. The processing section 22 stores the calculated phase shift distribution Φ (x, y) as the phase contrast image in the image storage 23.

Instead of using the two dimensional distribution φ (x, y) of the refraction angle, the two dimensional distribution ψ (x, y) of the phase shift value may be integrated along the x axis to generate the phase contrast image. The two dimensional distribution φ (x, y) of the refraction angle and the two dimensional distribution ψ (x, y) of the phase shift value correspond to a differential value of the phase shift distribution Φ (x, y). Therefore, both the two dimensional distribution φ (x, y) of the refraction angle and the two dimensional distribution ψ (x, y) of the phase shift value are phase differential images.

The above described fringe scanning and the generation processes of the phase contrast image are performed automatically under the control of the controller 20 after the operator instructs imaging using the input device 21. Finally, the phase contrast image of the object H is displayed on the monitor 24.

As described above, according to this embodiment, the distance $L_2$ between the first absorption grating 31 and the second absorption grating 32 can take any value. Setting the distance $L_2$ smaller than the minimum Talbot length for the Talbot interferometer allows the imaging unit 12 to have a low profile. In this embodiment, because most of the X-rays are not diffracted by the first absorption grating 31 and projected in a geometrical-optical manner, the irradiation X-ray does not require high spatial coherency. Accordingly, common X-ray sources used in the medical field can be used. In this embodiment, almost all the wavelength components of the irradiation X-ray contribute to the formation of the G1 image, which improves detection sensitivity of the phase contrast image. Thus, the image quality is improved.

As described in this embodiment, the phase contrast imaging of a patient in the standing position allows visualization of a slight tumor in chest lung field, a tumor in which soft tissues such as mediastinum and diaphragm are overlapped, and blood vessels which have been difficult to visualize using the conventional X-ray imaging apparatus. Thereby, more detailed diagnoses become possible. The phase contrast imaging of cervical spine, thoracolumbar regions, knee joints, and the like of the object H are performed under natural load. Accordingly, pathological conditions can be observed in detail.

Second Embodiment

Figure 15:
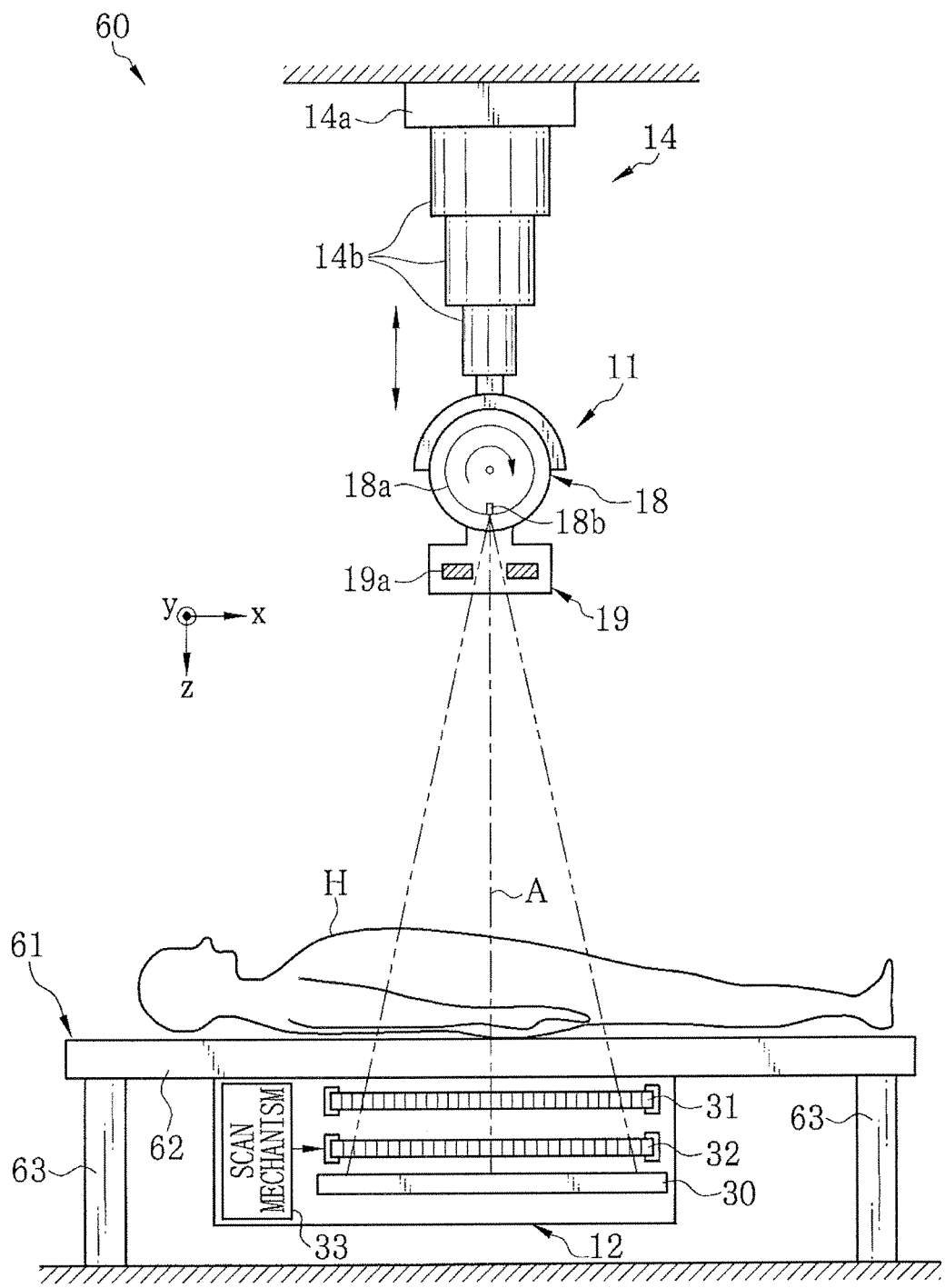
FIG. 15 is a schematic diagram showing an X-ray imaging system according to a second embodiment of the present invention.

FIG. 15 shows an X-ray imaging system 60 according to a second embodiment of the present invention. The X-ray imaging system 60 is an X-ray diagnostic apparatus for capturing an image of an object (patient) H in a lying position. The X-ray imaging system 60 is provided with the X-ray source 11, the imaging unit 12, and a bed or table 61 on which the object H lies down. The X-ray source 11 and the imaging unit 12 are similar to or the same as those in the first embodiment. The components thereof are designated by the same numerals as in the first embodiment. Hereafter, differences between the first and second embodiments are described. Other configuration and operation are the same as those in the first embodiment, so the descriptions thereof are omitted.

In this embodiment, the imaging unit 12 is mounted below a table top 62 to oppose the X-ray source 11 via the object H. The X-ray source 11 is held by the X-ray source holder 14. An angle change mechanism (not shown) of the X-ray source 11 sets the X-ray irradiation direction down. In this setting, the X-ray source 11 emits the X-ray to the object H lying down on the table top 62 of the table 61. The extension and the contraction of the column sections 14b of the X-ray source holder 14 move the X-ray source 11 in the up-and-down direction to adjust the distance L between the X-ray focal point 18b and the detection surface of the FPD 30.

As described above, the imaging unit 12 allows reducing the distance $L_2$ between the first absorption grating 31 and the second absorption grating 32 to have a low profile. Accordingly, table legs 63 for supporting the table top 62 of the table 61 can be shortened to make the table top 62 low. For example, it is preferable that the table top 62 is at the height of, for example, approximately 40 cm above the floor so that the object (patient) H can easily sit on it. Making the table top 62 low is preferable in ensuring a sufficient distance between the X-ray source 11 and the imaging unit 12.

Contrary to the above positional relationship between the X-ray source 11 and the imaging unit 12, the X-ray source 11 may be attached to the table 61 and the imaging unit 12 may be set on the ceiling side to capture an image of the object H in the lying position.

As described in this embodiment, capturing a phase contrast image of the object H in the lying position allows the image capture of lumbar spine, hip joint, and the like of the object H which are difficult to settle the position to capture the image. Appropriate fixing devices for fixing the object H to the table 61 may be used to reduce the deterioration of the phase contrast image caused by the body motion.

Third Embodiment

Figure 16:
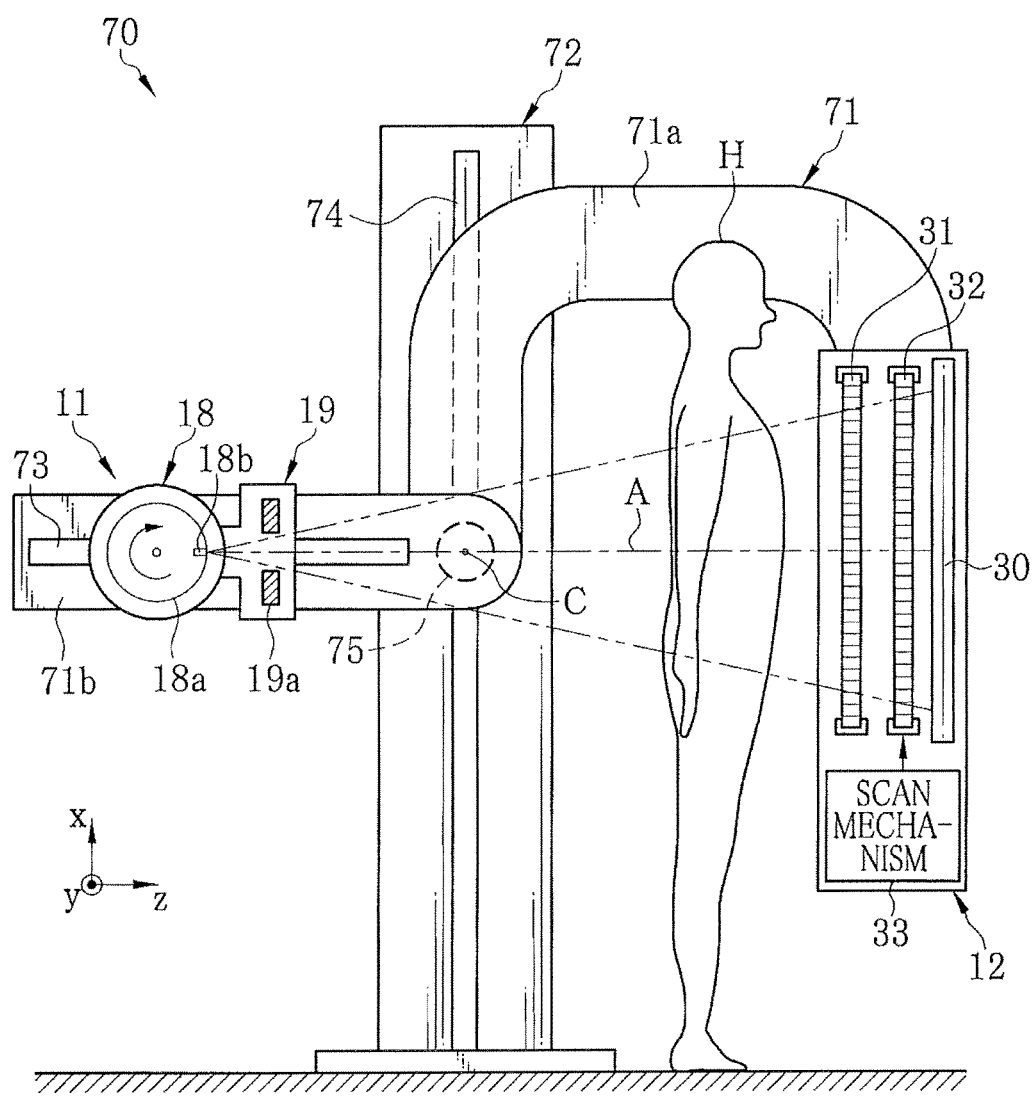
FIG. 16 is a schematic diagram showing an X-ray imaging system according to a third embodiment of the present invention.
Figure 17:
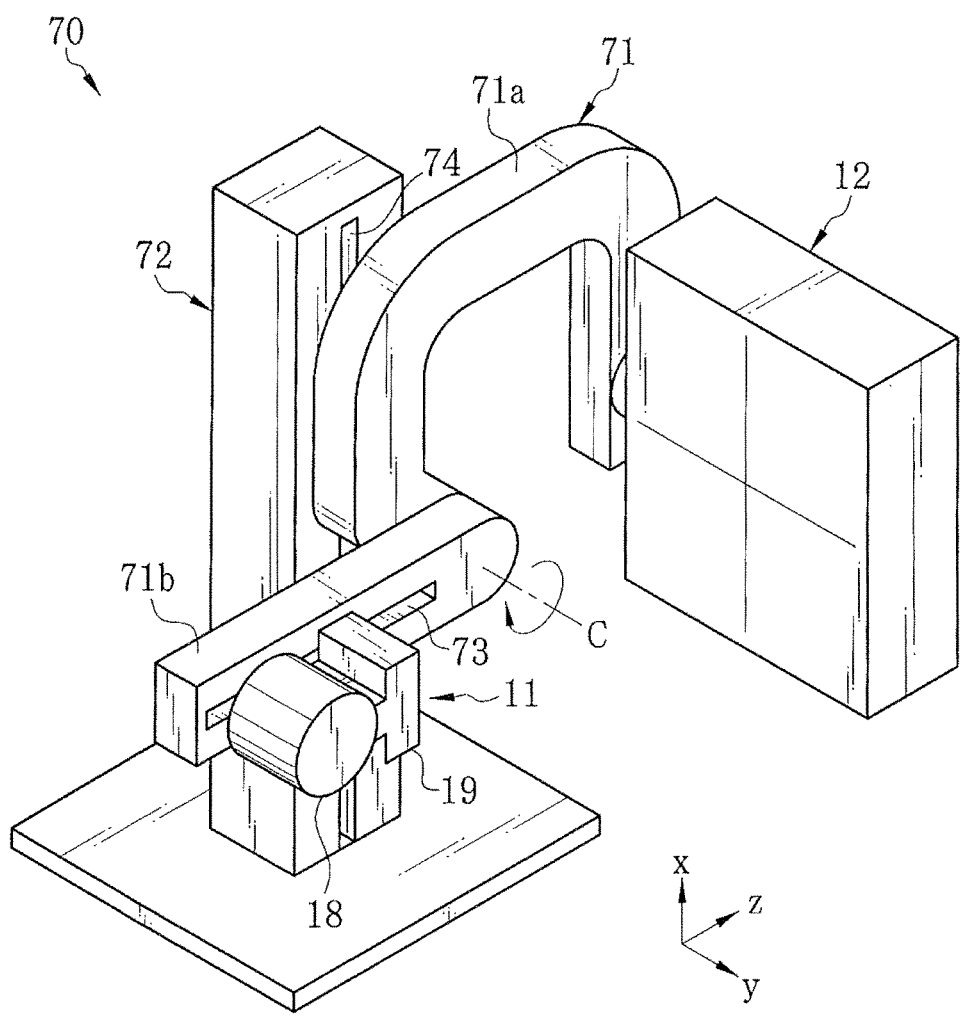
FIG. 17 is a perspective view showing an X-ray imaging system according to a third embodiment of the present invention.

FIGS. 16 and 17 show an X-ray imaging system 70 according to a third embodiment of the present invention. The X-ray imaging system 70 is an X-ray diagnostic apparatus capable of capturing images of the object (patient) H in standing and lying positions. A rotary arm 71 holds the X-ray source 11 and the imaging unit 12. The rotary arm 71 is coupled to an upright support 72 in a rotatable manner. The X-ray source 11 and the imaging unit 12 are similar to or the same as those in the first embodiment. The components thereof are designated by the same numerals as in the first embodiment. Hereafter, differences between the first and third embodiments are described. Other configuration and operation are same as those in the first embodiment, so descriptions thereof are omitted.

The rotary arm 71 is composed of a U-shaped section 71a shaped approximately like a letter U and a linear section 71b connected to one of the ends of the U-shaped section 71a. To the other end of the U-shaped section 71a, the imaging unit 12 is attached. A first groove 73 is formed in the linear section 71b along an extending direction of the linear section 71b. The X-ray source 11 is slidably attached to the first groove 73. The X-ray source 11 and the imaging unit 12 oppose each other. Moving the X-ray source 11 along the first groove 73 adjusts a distance between the X-ray focal point 18b and the detection surface of the FPD 30.

A second groove 74 is formed in the upright support 72 and extends along the up-and-down direction of the upright support 72. A connection mechanism 75 provided at connected portions of the U-shaped section 71a and the linear section 71b allows the rotary arm 71 to move along the second groove 74 in the up-and-down direction. The connection mechanism 75 also allows the rotary arm 71 to rotate about a rotation axis C extending in the y direction. Rotating the rotary arm 71 (in standing position as shown in FIG. 16) 90 degrees clockwise about the rotation axis C and placing the imaging unit 12 below the table (not shown) on which the object H lies down allow the imaging of the object H in the lying position. The rotary arm 71 can be rotated at any angle other than 90 degrees. The object H can be imaged at any direction or angle other than the standing position (horizontal direction) and the lying position (up-and-down direction).

In this embodiment, the rotary arm 71 holds the X-ray source 11 and the imaging unit 12. Accordingly, it becomes easy to set the distance between the X-ray source 11 and the imaging unit 12 with high accuracy compared to the above-described first and second embodiments.

In this embodiment, the imaging unit 12 is attached to the U-shaped section 71a and the X-ray source 11 is attached to the linear section 71b. Alternatively, like an X-ray diagnostic apparatus using a so-called C arm, the imaging unit 12 may be attached to one end of the C arm and the X-ray source 11 may be attached to the other end.

Fourth Embodiment

Figure 18:
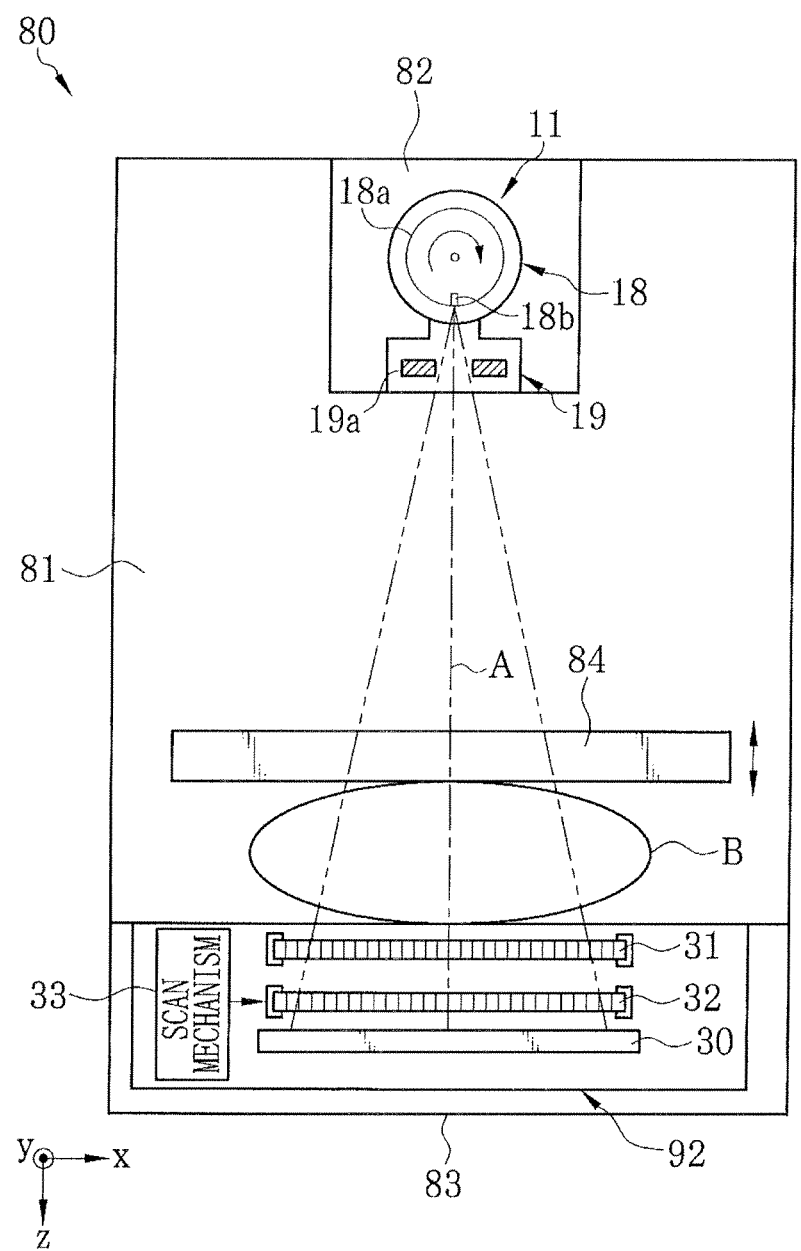
FIG. 18 is a schematic front view showing a mammography apparatus according to a fourth embodiment of the present invention.
Figure 19:
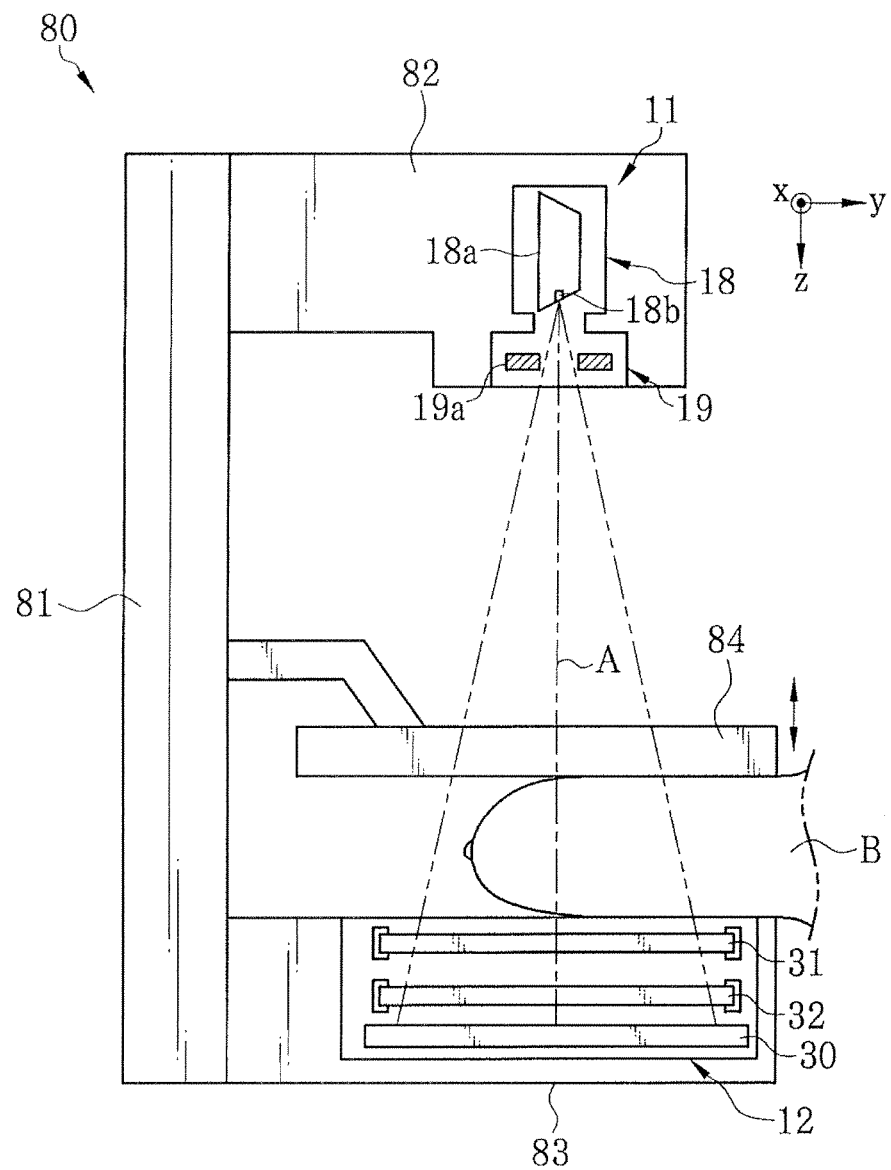
FIG. 19 is a schematic lateral view showing a mammography apparatus according to a fourth embodiment of the present invention.

Next, an example in which the present invention is applied to mammography (X-ray breast imaging) is described. Mammography apparatuses 80 shown in FIGS. 18 and 19 are apparatuses for capturing phase contrast images of a breast B as an object. Each mammography apparatus 80 is provided with a supporting section 81 rotatably coupled to a support (not shown), an X-ray source housing 82 arranged at an end of the supporting section 81, an imaging table 83 arranged at the other end of the supporting section 81, and a compression plate 84 movable in the up-and-down direction relative to the imaging table 83.

The X-ray source 11 is housed in the X-ray source housing 82. The imaging table 83 incorporates the imaging unit 12. The X-ray source 11 and the imaging unit 12 oppose each other. A moving mechanism (not shown) moves the compression plate 84 to compress the breast B between the compression plate 84 and the imaging table 83. The X-ray imaging of the breast B is performed while the breast B is compressed.

The X-ray source 11 and the imaging unit 12 are similar to or the same as those in the first embodiment. The components thereof are designated by the same numerals as in the first embodiment. Other configuration and operation are the same as those in the first embodiment, so the descriptions thereof are omitted.

Fifth Embodiment

Figure 20:
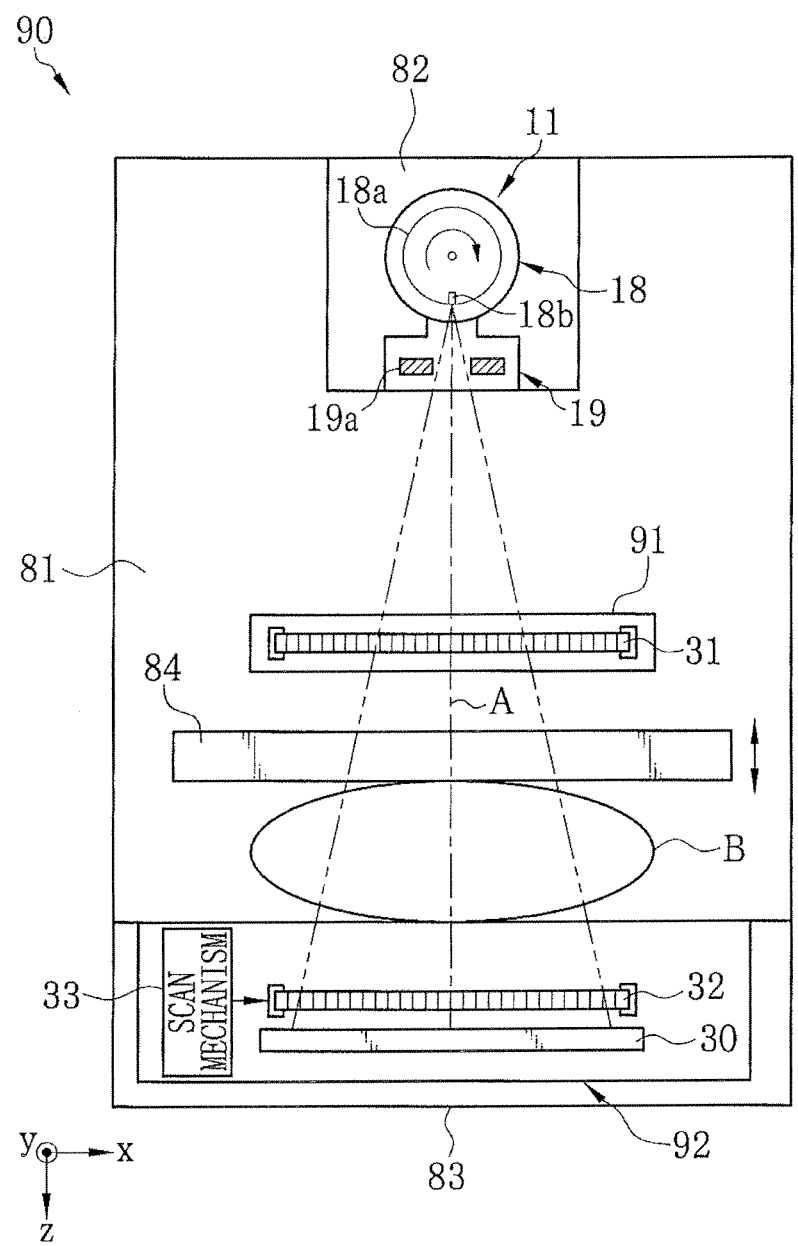
FIG. 20 is a schematic front view showing a mammography apparatus according to a fifth embodiment of the present invention.

Next, an altered example of the above-described mammography apparatus is described. A mammography apparatus 90 shown in FIG. 20 only differs from the mammography apparatus 80 of the fourth embodiment in that the first absorption grating 31 is arranged between the X-ray source 11 and the compression plate 84. The first absorption grating 31 is housed in a grating housing 91 connected to the supporting section 81. An imaging unit 92 is not provided with the first absorption grating 31. The imaging unit 92 is composed of the FPD 30, the second absorption grating 32, and the scan mechanism 33.

The G1 image formed at the position of the second absorption grating 32 is deformed by the object B even if the object (breast) B is located between the first absorption grating 31 and the second absorption grating 32. Accordingly, the intensity modulated signal is phase-shifted by the object B and thus the phase contrast image of the object B is obtained using the above-described principle.

In this embodiment, the object B is irradiated with the X-ray dose reduced to approximately half due to the shield of the first absorption grating 31. Thereby, the exposure dose of the object B is reduced to approximately half the exposure dose in the fourth embodiment. An object can be arranged between the first absorption grating 31 and the second absorption grating 32 as described in this embodiment not only in the mammography apparatus but also in other X-ray imaging systems.

Sixth Embodiment

Figure 21:
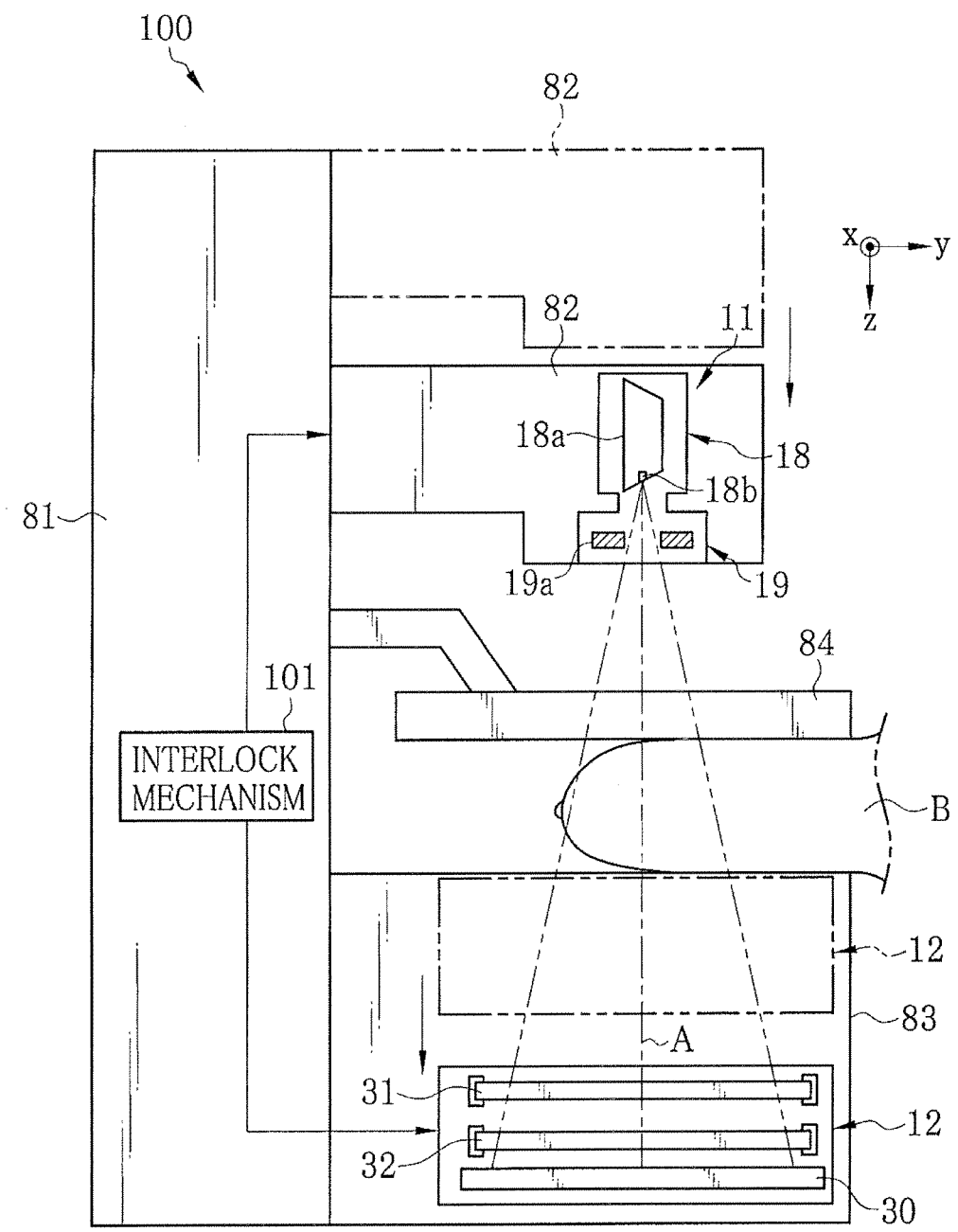
FIG. 21 is a schematic lateral view showing a mammography apparatus according to a sixth embodiment of the present invention.

Next, FIG. 21 shows a mammography apparatus 100 capable of performing magnification radiography of the object B. The mammography apparatus 100 is provided with an interlocking movement mechanism 101 for moving the X-ray source housing 82 and the imaging unit 12 in an interlocking manner. The interlocking movement mechanism 101 is controlled by the controller 20. The interlocking movement mechanism 101 moves the X-ray source housing 82 and the imaging unit 12 in the z direction while the relative positions of the first absorption grating 31, the second absorption grating 32, and the FPD 30 are kept unchanged.

The position of the object B is fixed by the imaging table 83 and the compression plate 84. When the X-ray source housing 82 and the imaging unit 12 are moved downward, the object B becomes closer to the X-ray source 11, and thereby the magnification radiography of the object B is performed. The magnification can be inputted using the input device 21. When the magnification is inputted using the input device 21, the controller 20 controls the interlocking movement mechanism 101 to move the X-ray source housing 82 and the imaging unit 12 to set the distance between the object B and the imaging table 83 in accordance with the inputted magnification.

For example, for the diagnosis of breast cancer, a positional relationship between calcification or mass and mammary gland structure is important. To diagnose a suspicious lesion with higher accuracy, it is necessary to improve image resolution. In this case, the magnification radiography using the mammography apparatus 100 of this embodiment is effective. Other configuration and operation are same as those in the fourth embodiment, so the descriptions are omitted.

Seventh Embodiment

Figure 22:
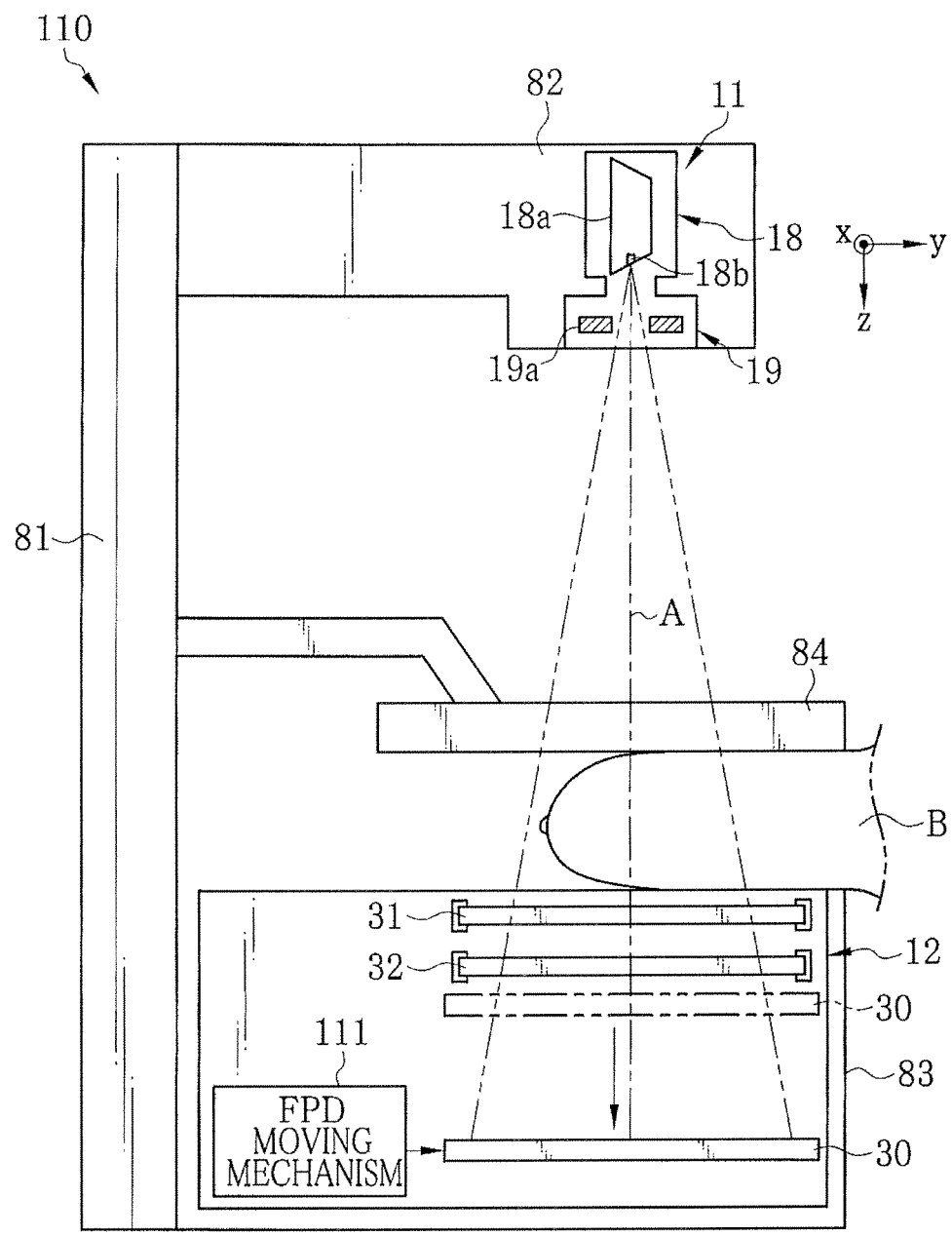
FIG. 22 is a schematic lateral view showing a mammography apparatus according to a seventh embodiment of the present invention.

Next, FIG. 22 shows a mammography apparatus 110 of this embodiment capable of performing magnification radiography of the object B. The mammography apparatus 110 is provided with an FPD moving mechanism 111 for moving the FPD 30 in the z direction. An image incident on the FPD 30 is enlarged as the FPD 30 is moved away from the X-ray source 11, and thereby the magnification radiography of the object B is performed. The controller 20 controls the FPD moving mechanism 111 to move the FPD 30 to a position in accordance with the magnification inputted through the input device 21. Other configuration and operation are the same as those in the above fourth embodiment, so the descriptions thereof are omitted.

Eighth Embodiment

Figure 23:
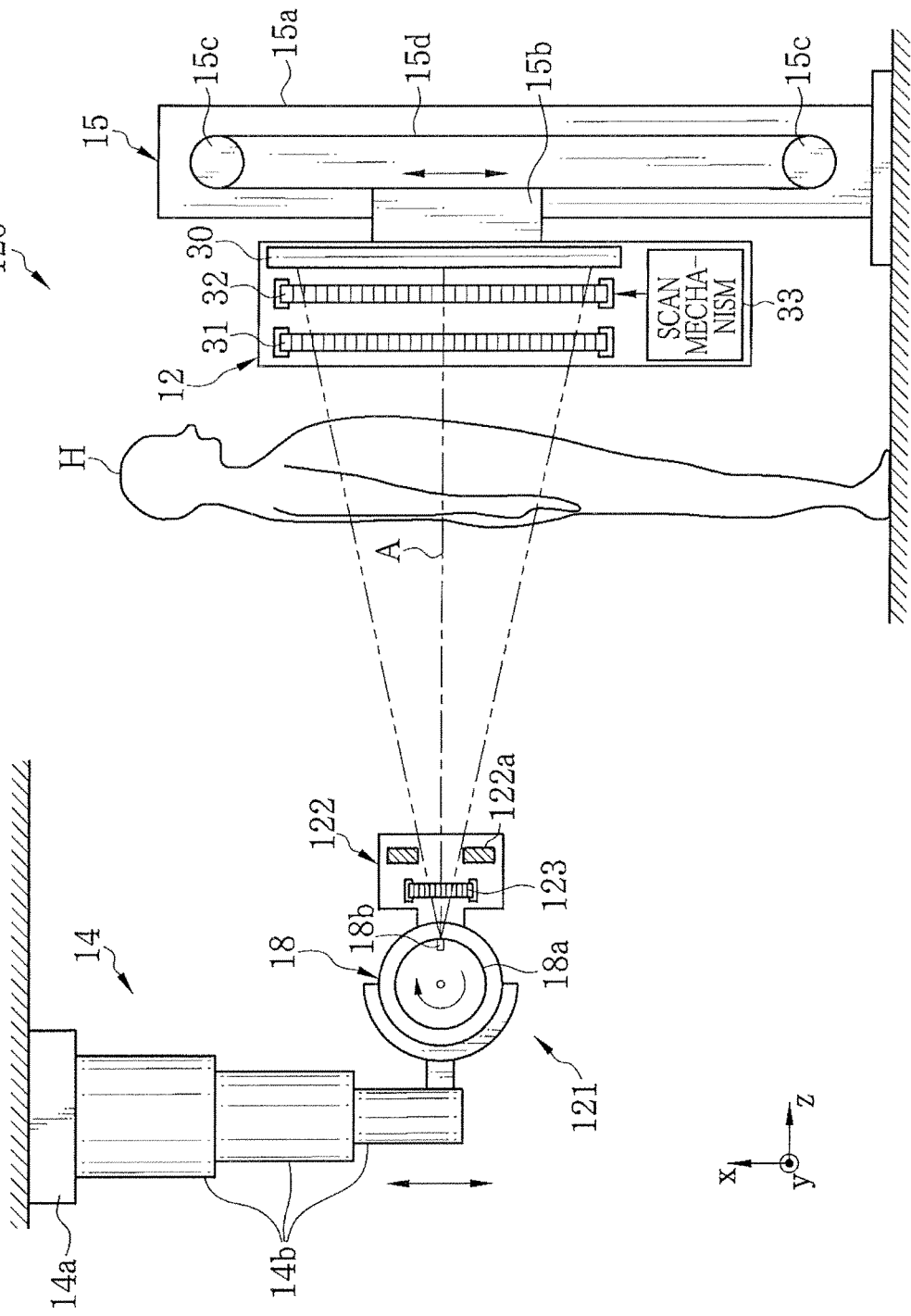
FIG. 23 is a schematic diagram showing an X-ray imaging system according to an eighth embodiment of the present invention.

FIG. 23 shows an X-ray imaging system 120 according to an eighth embodiment of the present invention. The X-ray imaging system 120 differs from the X-ray imaging system 10 of the first embodiment in that a multi-slit 123 is provided in a collimator unit 122 of the X-ray source 121. Other configuration is the same as that in the first embodiment, so the description thereof is omitted.

In the first embodiment, when the distance between the X-ray source 11 and the FPD 30 is set at a setting (1 m to 2 m) used in a radiography room of a common hospital, blur of the G1 image caused by the size of the X-ray focal point 18b (generally, around 0.1 mm to 1 mm) may degrade the image quality of the phase contrast image. In this case, a pinhole may be provided in the immediate vicinity of the X-ray focal point 18b to effectively decrease the focal point size. When an aperture area of the pinhole is decreased to reduce the effective focal point size, the X-ray intensity drops. To solve this problem, in this embodiment, the multi-slit 123 is arranged in the immediate vicinity of the X-ray focal point 18b.

The multi-slit 123 is an absorption grating (third absorption grating) having a similar or the same configuration as the first and the second absorption gratings 31 and 32 provided in the imaging unit 12. The multi-slit 123 has X-ray shield members extending in one direction (y direction) and periodically arranged in the same direction (x direction) as the X-ray shield members 31b and 32b of the first and second absorption gratings 31 and 32. By partially shielding the radiation emitted from the X-ray focal point 18b, the multi-slit 123 reduces the effective focal point size in the x direction to form a plurality of point light sources (dispersed light sources) in the x direction. In this embodiment, relative to the z direction, the position of the multi-slit 123 is the position of the X-ray focal point.

The grating pitch $p_3$ of the multi-slit 123 needs to be set to satisfy a mathematical expression (17) where $L_3$ denotes the distance between the multi-slit 123 and the first absorption grating 31.

$$p_3 = \frac{L_3}{L_2} p_2 \quad (17)$$

In this embodiment, the position of the multi-slit 123 is virtually the position of the X-ray focal point. Accordingly, the grating pitch $p_2$ and the opening width $d_2$ of the second absorption grating 32 are determined to satisfy mathematical expressions (18) and (19).

$$p_2 = \frac{L_3 + L_2}{L_3} p_1 \quad (18)$$

$$d_2 = \frac{L_3 + L_2}{L_3} d_1 \quad (19)$$

In this embodiment, to ensure the length V of the effective field of view in the x direction of the detection surface of the FPD 30, the thicknesses $h_1$ and $h_2$ of the X-ray shield members 31b and 32b of the first and second absorption gratings 31 and 32 are determined to satisfy mathematical expressions (20) and (21) where L' denotes a distance between the multi-slit 123 and the detection surface of the FPD 30.

$$h_1 \leq \frac{L'}{V/2} d_1 \quad (20)$$

$$h_2 \leq \frac{L'}{V/2} d_2 \quad (21)$$

The mathematical expression (17) represents a geometric condition to coincide (superpose) each of the G1 images of the X-ray, emitted from each of the point light sources formed dispersedly by the multi-slit 123, at the position of the second absorption grating 32. In this embodiment, because the G1 images based on the point light sources formed by the multi-slit 123 are superposed with each other, the image quality of the phase contrast image is improved without degrading the X-ray intensity.

The above-described multi-slit 123 is not limited to the first embodiment and applicable to any of the above embodiments.

Ninth Embodiment

As described in the first embodiment, the phase contrast image is based on a refractive component of the X-ray in the periodic arrangement direction (x direction) of the X-ray shield members 31b and 32b of the first and second absorption gratings 31 and 32. The phase contrast image does not include a refractive component in the extending direction (y direction) of the X-ray shield members 31b and 32b. For this reason, a body part which cannot be visualized exists depending on the shape and orientation of the object H. For example, when the weight-bearing surface of articular cartilage is in the y direction, it is considered that cartilage surrounding tissues (such as tendons and ligaments) having the shape vertical to the weight-bearing surface are not visualized sufficiently. An image of the insufficiently-visualized body part can be retaken again after the object H is moved. This, however, increases physical stress of the object H and the burden of the operator. In addition, it is difficult to ensure the positional reproducibility of the retaken image.

Figure 24A:
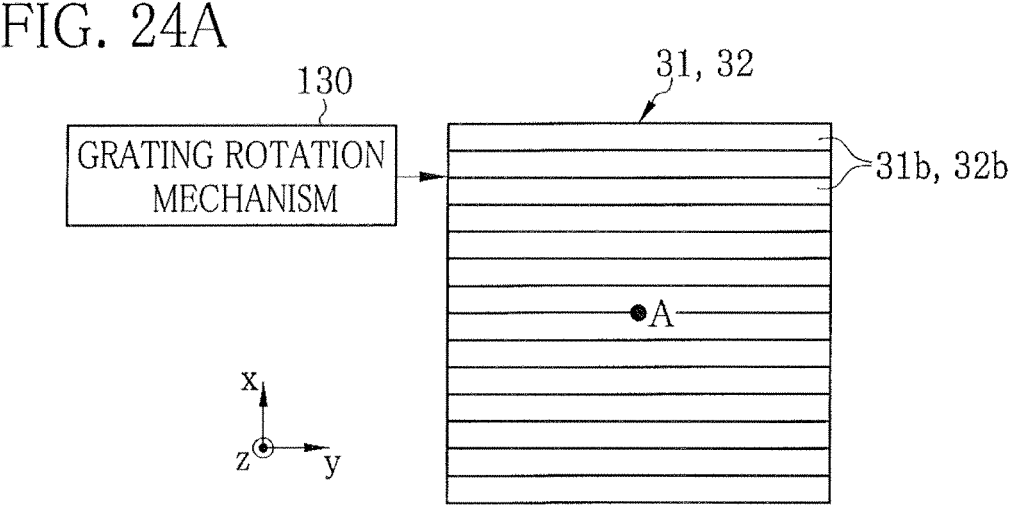
FIGS. 24A and 24B are schematic diagrams describing a grating rotation mechanism used in a ninth embodiment of the present invention.
Figure 24B:
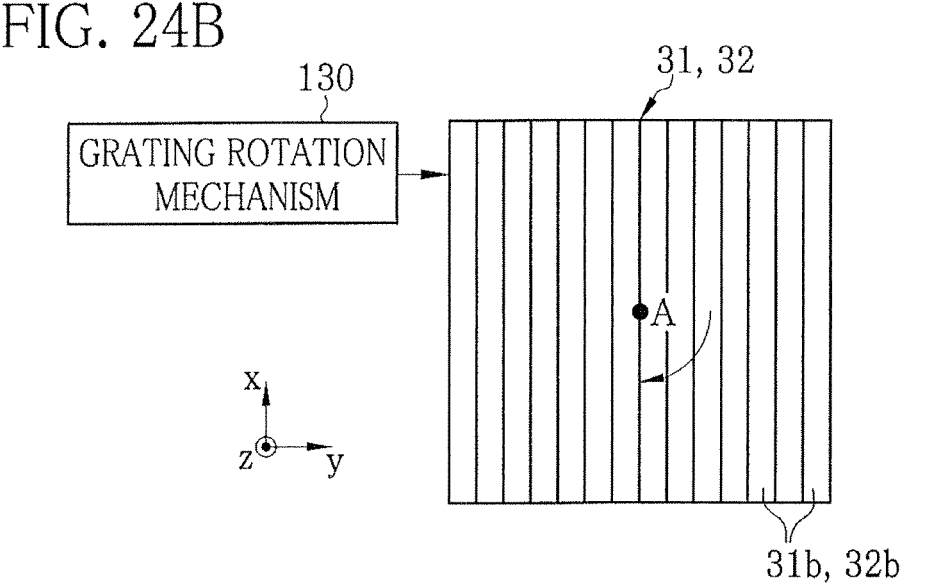

In the ninth embodiment, as shown in FIGS. 24A and 24B, it is suitable to provide a grating rotation mechanism 130 for integrally rotating the first and second absorption gratings 31 and 32 90° about a virtual line (an optical axis A of the X-ray), orthogonal to centers of the grating surfaces of the first and second absorption gratings 31 and 32, from a first orientation (the direction where the X-ray shield members 31b and 32b extend in the y direction) shown in FIG. 24A to a second orientation (the direction where the X ray shield members 31b and 32b extend in the x direction) shown in FIG. 24B. It is suitable to perform the operation and processes similar to or the same as those described above for each of the first and second orientations to generate a phase contrast image.

The grating rotation mechanism 130 may rotate the first and second absorption gratings 31 and 32 integrally but independently of the FPD 30. The grating rotation mechanism 130 may rotate the first absorption grating 31, the second absorption grating 32, and the FPD 30 integrally. The rotation angle is not limited to 90°. There is no restraint on the rotation angle. The generation of the phase contrast image in the first and second orientations using the grating rotation mechanism 130 is applicable to any of the above embodiments.

10th Embodiment

Figure 25:
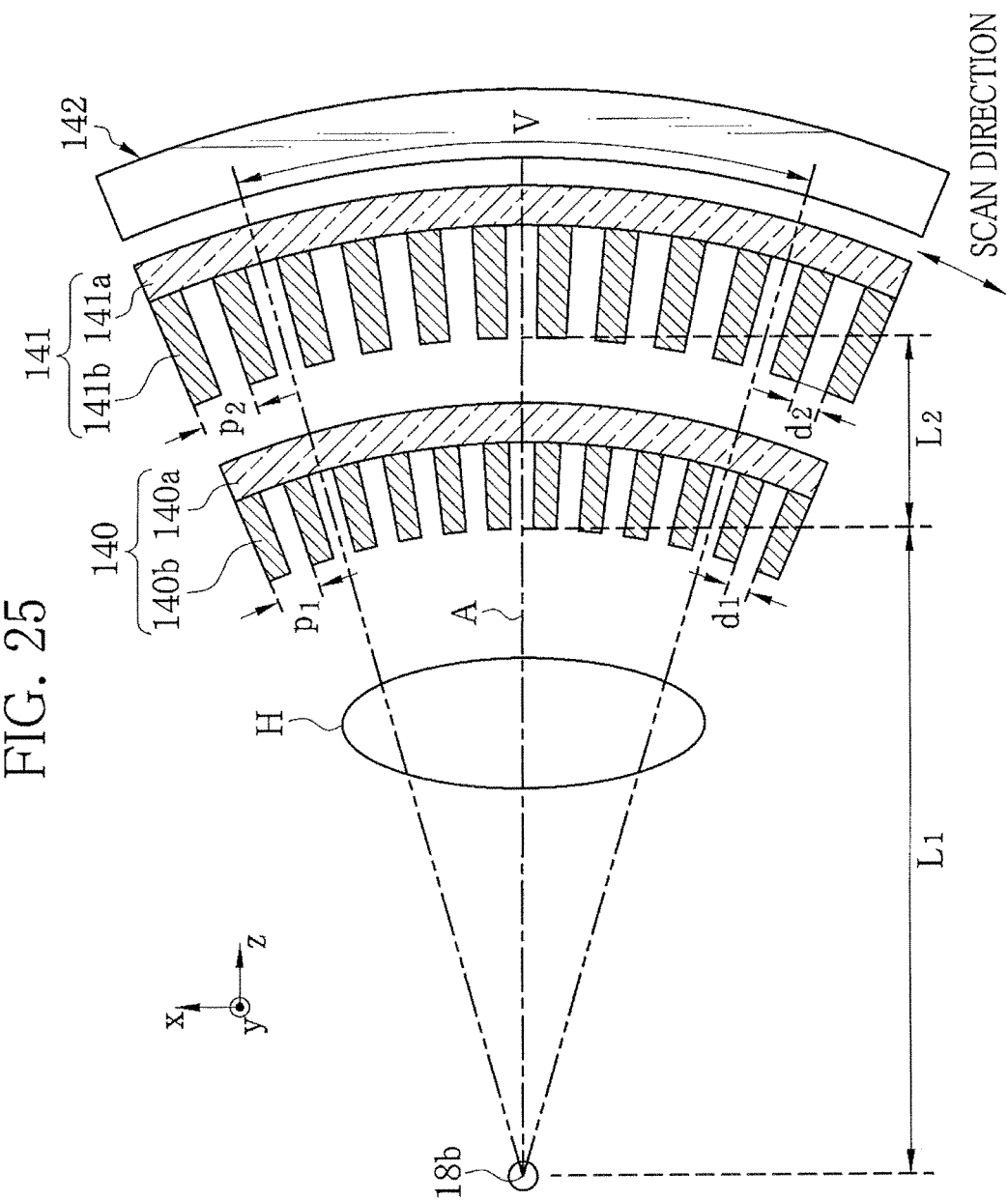
FIG. 25 is schematic diagram showing an X-ray imaging system according to a 10th embodiment of the present invention.

The first and second absorption gratings 31 and 32 of the first embodiment are configured such that the directions of the periodic arrangements of the X-ray shield members 31b and 32b are linear (namely, the grating surfaces are flat). Alternatively, as shown in FIG. 25, it is suitable to use first and second absorption gratings 140 and 141 having curved concave grating surfaces.

The first absorption grating 140 has X-ray shield members 140b periodically arranged at a predetermined pitch $p_1$ on a surface of a substrate 140a. The substrate 140a is X-ray transmissive and curved. Each of the X-ray shield members 140b extends linearly in the y direction as in the first embodiment. A grating surface of the first absorption grating 140 has a shape formed along a cylindrical surface having a line passing through X-ray focal point 18b and extending in the extending direction of the X-ray shield members 140b as the center axis. Likewise, the second absorption grating 141 has X-ray shield members 141b periodically arranged at a predetermined pitch $p_2$ on a surface of a substrate 141a. The substrate 141a is X-ray transmissive and curved. Each of the X-ray shield members 141b extends linearly in the y direction. A grating surface of the second absorption grating 141 has a shape formed along a cylindrical surface having a line passing through X-ray focal point 18b and extending in the extending direction of the X-ray shield members 141b as the center axis.

The grating pitch $p_2$ and opening width $d_2$ are determined to satisfy the mathematical expression (1) where $L_1$ denotes a distance between the X-ray focal point 18b and the first absorption grating 140 and $L_2$ denotes a distance between the first absorption grating 140 and the second absorption grating 141. The opening widths $d_1$ of the slits of the first absorption grating 140 and the opening widths $d_2$ of the slits of the second absorption grating 141 are determined to satisfy the mathematical expression (2).

Thus, by forming the grating surfaces of the first and second absorption gratings 140 and 141 in cylindrical surfaces, all the X-ray emitted from the X-ray focal point 18b enters the grating surfaces orthogonally when the object H is absent. In this embodiment, there are no upper limits on the thickness $h_1$ of the X-ray shield members 140b and the thickness $h_2$ of the X-ray shield members 141b. There is no need to consider the mathematical expressions (5) and (6).

In this embodiment, one of the first and second absorption gratings 140 and 141 is moved in a direction along the grating surface (cylindrical surface) about the X-ray focal point 18b as the center to perform the above described fringe scanning. In this embodiment, it is preferable to use an FPD 142 whose detection surface is cylindrical. Likewise, the detection surface of the FPD 142 is a cylindrical surface having a straight line, passing through the X-ray focal point 18b and extending in the y direction, as the center axis.

The first absorption grating 140, the second absorption grating 141, and the FPD 142 of this embodiment are applicable not only to the first embodiment but also to any of the above embodiments. Furthermore, it is suitable for the multi-slit 123 described in the eighth embodiment to have the shape similar to or the same as the shapes of the first and second absorption gratings 140 and 141.

Each of the first and second absorption gratings 140 and 141 may be formed with planar grating modules joined to each other. The substrates 140a and 141a of the first and second absorption gratings 140 and 141 may be flexible.

It is preferable to make the FPD 142 flexible and provide an SID changing mechanism for changing the distance (SID is an abbreviation for Source to Image Distance) between the X-ray focal point 18b (Source) and the detection surface of the FPD 142 (Image) and a curvature adjustment mechanism for changing the curvature in accordance with the SID. The SID value can be inputted using the input device 21, for example. Based on the inputted SID value, the controller 20 controls the SID changing mechanism to adjust the position of the X-ray focal point 18b or the FPD 142 and controls the curvature adjustment mechanism to change the curvature of the FPD 142 such that the X-ray incident direction becomes approximately normal to the detection surface.

Figure 26:
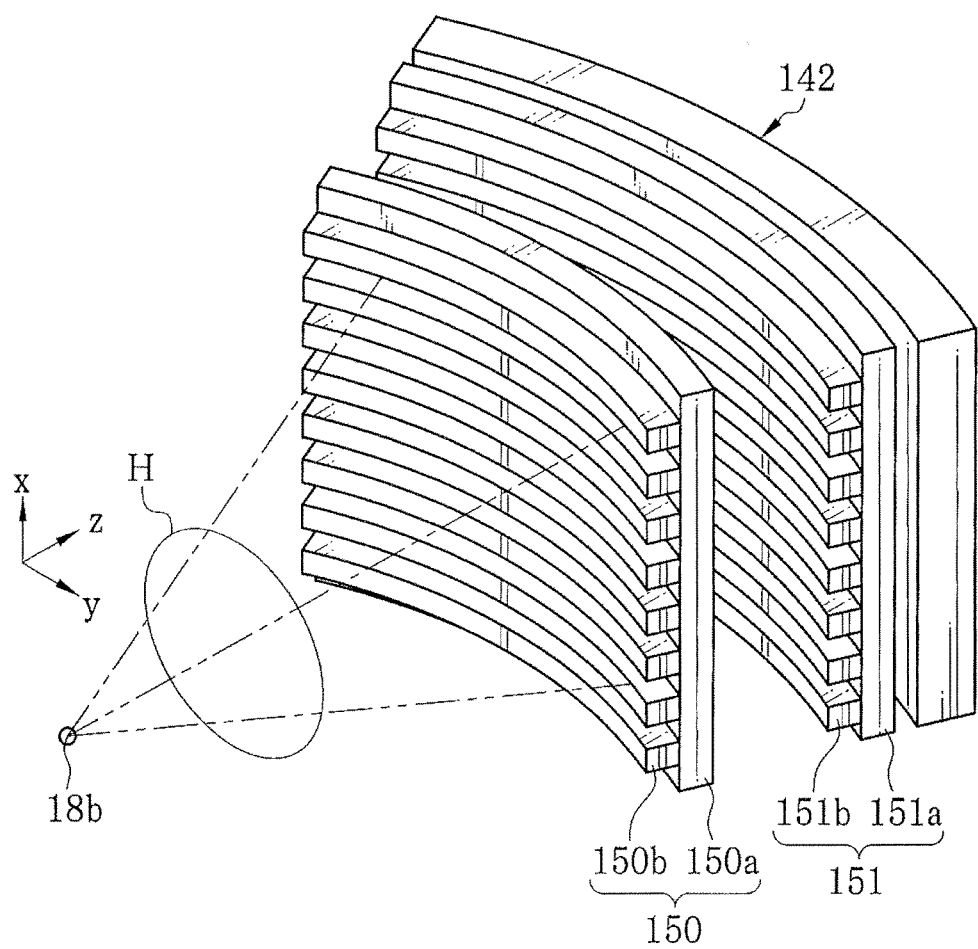
FIG. 26 is schematic diagram showing an X-ray imaging system according to an 11th embodiment of the present invention.

When the distances $L_1$ and $L_2$ change in accordance with the change in the SID changed by the SID changing mechanism, it is preferable to provide a mechanism to change the curvatures of the first and second absorption gratings 140 and 141 in accordance with the distances $L_1$ and $L_2$. When the changes in the distances $L_1$ and $L_2$ are large, however, the grating pitches $p_1$ and $p_2$ cannot keep up with the changes in the distances $L_1$ and $L_2$ even if the curvatures of the first and second absorption gratings 140 and 141 are changed. In this case, it is preferable to make the first and second absorption gratings 140 and 141 replaceable with those having the appropriate curvatures and grating pitches $p_1$ and $p_2$ 11th Embodiment In the above $10^{th}$ embodiment, the first absorption grating 140 is configured by arranging the X-ray shield members 140b in a direction orthogonal to a direction of the curve of the substrate 140a. The second absorption grating 141 is configured by arranging the X-ray shield members 141b in a direction orthogonal to a direction of the curve of the substrate 141a. Thereby, the restriction of the thicknesses of the X-ray shield members 140b and 141b is eliminated. As shown in FIG. 26, it is preferable to configure the first absorption grating 150 by arranging the X-ray shield members 150b along a direction of the curve of a substrate 150a, and to configure the second absorption grating 151 by arranging the X-ray shield members 151b along a direction of the curve of a substrate 151a (namely, the X-ray shield members 150b and 151b are curved).

In the above $10^{th}$ embodiment, the relative scanning of the first and second absorption gratings 140 and 141 needs to be performed along a circular orbit about the X-ray focal point 18b as the center. In this embodiment, the scanning direction may be a direction (x-direction) orthogonal to the direction of the curve, that is, a linear path. Accordingly, the scan mechanism is realizable with a simple mechanism using a guide rail for a linear motion and an actuator such as a pulse motor. Other configuration and operation are similar to or the same as those described in the above 10$^{th}$ embodiment, so the descriptions thereof are omitted.

12th Embodiment

In each of the above embodiments, the second absorption grating is provided independently of the FPD. With the use of an FPD disclosed in Japanese Patent Laid-Open Publication No. 2009-133823, the second absorption grating can be eliminated. The FPD is a direct conversion type FPD provided with a conversion layer for converting the X-ray into electric charge and charge collection electrodes for collecting the converted electric charge. The charge collection electrode in each pixel is composed of linear electrode groups arranged to have mutually different phases. Each linear electrode group is composed of linear electrodes arranged at a predetermined period and electrically connected to each other. The charge collection electrode constitutes the intensity modulator.

Figure 27:
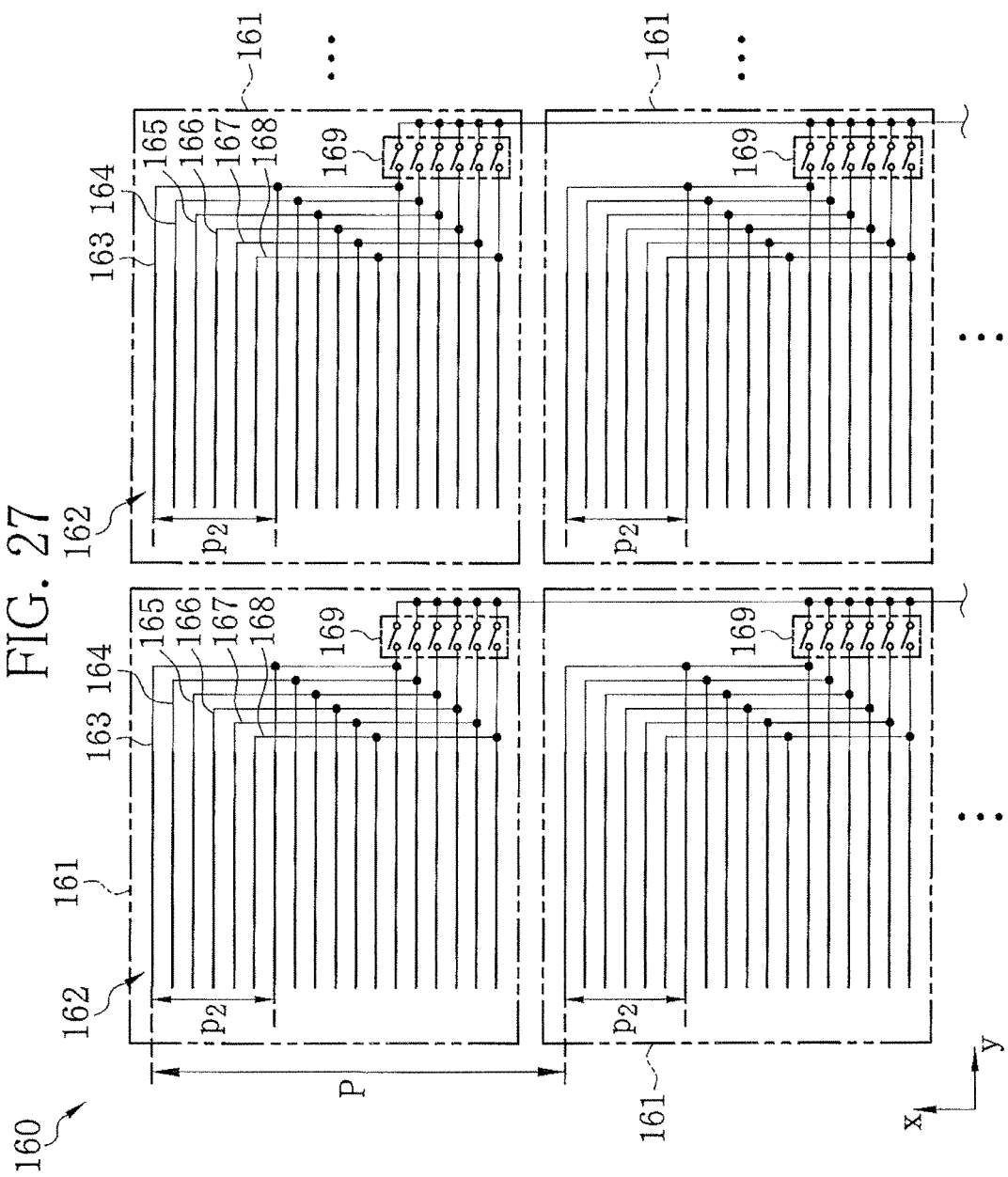
FIG. 27 is a schematic diagram showing an X-ray detector used in a 12th embodiment of the present invention.

In FIG. 27, an FPD 160 of this embodiment is composed of pixels 161 arranged in two dimensions at a constant pitch along x and y directions. Each pixel 161 has a charge collection electrode 162 for collecting electric charge converted by the conversion layer that converts X-ray into electric charge. The charge collection electrode 162 is composed of first to sixth linear electrode groups 163 to 168. The phase of the arrangement period of each linear electrode group is shifted by $\pi/3$. To be more specific, when the phase of the first linear electrode group 163 is determined to be zero, the phase of the second linear electrode group 164 is $\pi/3$; the phase of the third linear electrode group 165 is $2\pi/3$; the phase of the fourth linear electrode group 166 is $\pi$; the phase of the fifth linear electrode group 167 is $4\pi/3$; the phase of the sixth linear electrode group 168 is $5\pi/3$.

Each of the first to sixth linear electrode groups 163 to 168 has linear electrodes extending in the y direction and periodically arranged at a predetermined pitch $p_2$.

Each pixel 161 is further provided with a switch group 169 for reading the electric charge collected by the charge collection electrode 162. The switch group 169 is composed of TFT switches respectively provided to the first to the sixth linear electrode groups 163 to 168. The switch group 169 is controlled to separately read the electric charge collected by each of the first to the sixth linear electrode groups 163 to 168. Thereby, six different fringe images with mutually different phases are obtained based on the G2 image (fringe image) per image capture. The phase contrast image is produced based on the six different fringe images.

Using the FPD 160 of this embodiment eliminates the need for the second absorption grating 32 in the imaging unit. As a result, cost is reduced and the imaging unit with the lower-profile is obtained. In this embodiment, fringe images having different phases are obtained by single exposure. Accordingly, mechanical scanning for the fringe-scanning is unnecessary and thus the scan mechanism 33 is eliminated. Other than the above charge collection electrodes, the charge collection electrodes having configurations disclosed in the Japanese Patent Laid-Open Publication No. 2009-133823 can be used.

13th Embodiment

In each of the above embodiments, a series of image captures is performed while the X-ray source and the imaging unit are fixed to obtain one phase contrast image. Several phase contrast images may be also obtained while the X-ray source and the imaging unit are translationally moved to several positions in one of the directions orthogonal to the optical axis A. In this case, along image larger than the size of the detection surface of the FPD can be generated by stitching the obtained phase contrast images partly overlapped with each other.

Figure 28:
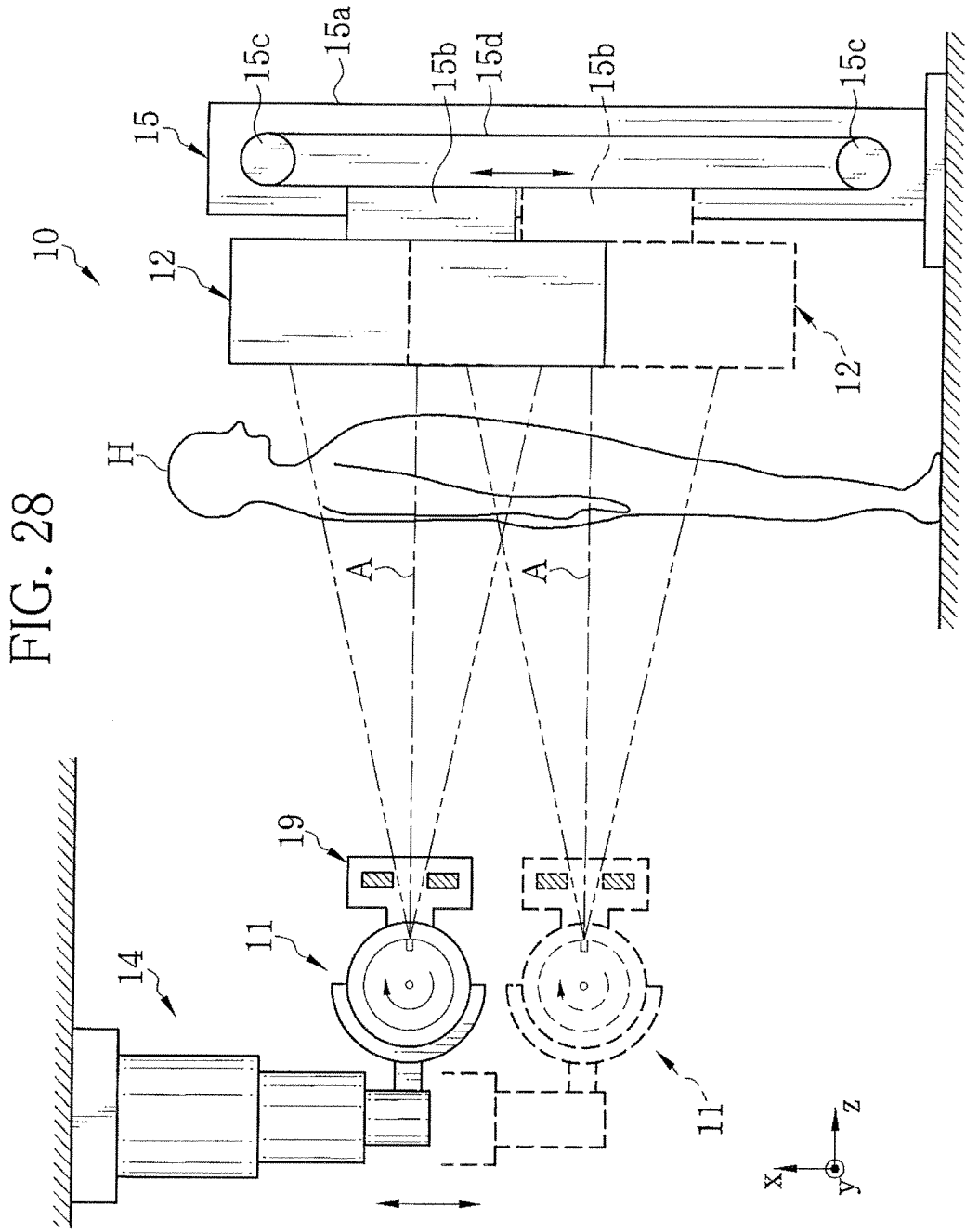
FIG. 28 is a schematic diagram of an X-ray imaging system according to a 13th embodiment of the present invention.

For example, for the X-ray imaging system 10 of the first embodiment that performs imaging of a patient in the standing position, as shown in FIG. 28, the X-ray source holder 14 and the upright stand 15 are controlled to move the X-ray source 11 and the imaging unit 12 in an interlocking manner in the up-and-down direction to translationally move the X-ray source 11 and the imaging unit 12 in a direction orthogonal to the optical axis A of the X-ray. In the third embodiment, moving the rotary arm 71 along the groove 74 of the upright support 72 allows the above described translational movement. For the second, fourth, and fifth embodiments, there is no mechanism to translationally move the X-ray source and the imaging unit. Accordingly, a mechanism for translationally moving the X-ray source and the imaging unit in the direction orthogonal to the optical axis A may be provided as described above.

It is preferable to perform the imaging while the X-ray source and the imaging unit are moved in two dimensions in x and y directions to generate a long image in which the phase contrast images are stitched in two dimensional directions.

14th Embodiment

In each of the above embodiments, the two-dimensional phase contrast image is obtained as an example. The phase contrast image allows visualization of soft tissues such as muscle-tendon and blood vessels which have been difficult to visualize using the conventional X-ray imaging. In a two-dimensional plain image, however, this visualization may rather create obstruction shadow for imaging diagnosis.

Figure 29:
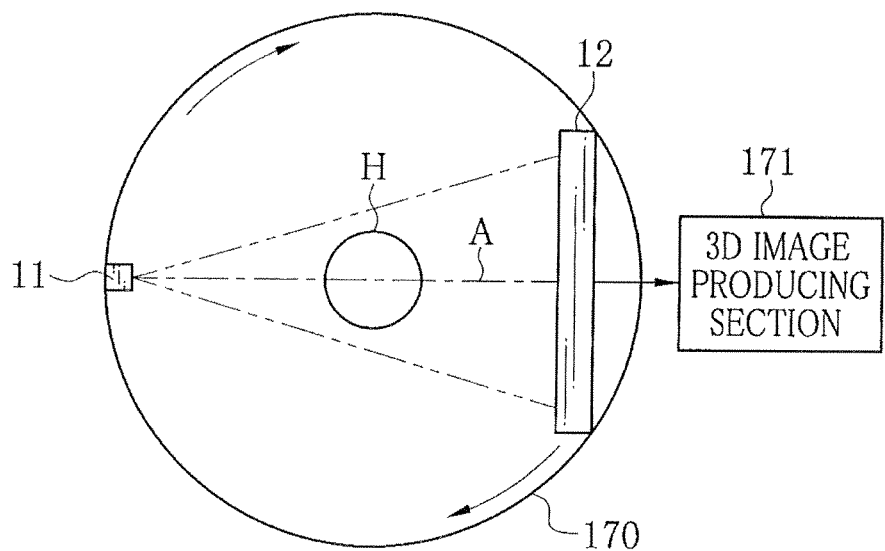
FIG. 29 is a schematic diagram showing an X-ray phase CT apparatus according to a 14th embodiment of the present invention.

To separate the obstruction shadow to perform correct image interpretation and diagnosis, it is preferable to apply the present invention to the X-ray phase CT apparatus for obtaining three-dimensional image. To be more specific, as shown in FIG. 29, a rotational movement mechanism 170 is provided. The rotational movement mechanism 170 rotates the X-ray source 11 and the imaging unit 12 integrally in the direction of the arrow shown in FIG. 29 relative to the object H arranged between the X-ray source 11 and the imaging unit 12. Based on the phase contrast images of the object H obtained by the imaging unit 12 at different rotation angles rotated by the rotational movement mechanism 170, a 3D image reconstruction section 171 produces a three-dimensional image of the object H.

A method for producing a three-dimensional image based on two or more images is similar to or the same as a conventional X-ray CT apparatus. In this embodiment, as with the fifth embodiment, the object H may be arranged between the first absorption grating and the second absorption grating. Instead of the X-ray source 11, the X-ray source 121 of the eighth embodiment may be used. It is preferable to obtain one phase contrast image by single exposure using the FPD 160 of the 12$^{th}$ embodiment.

15th Embodiment

Figure 30:
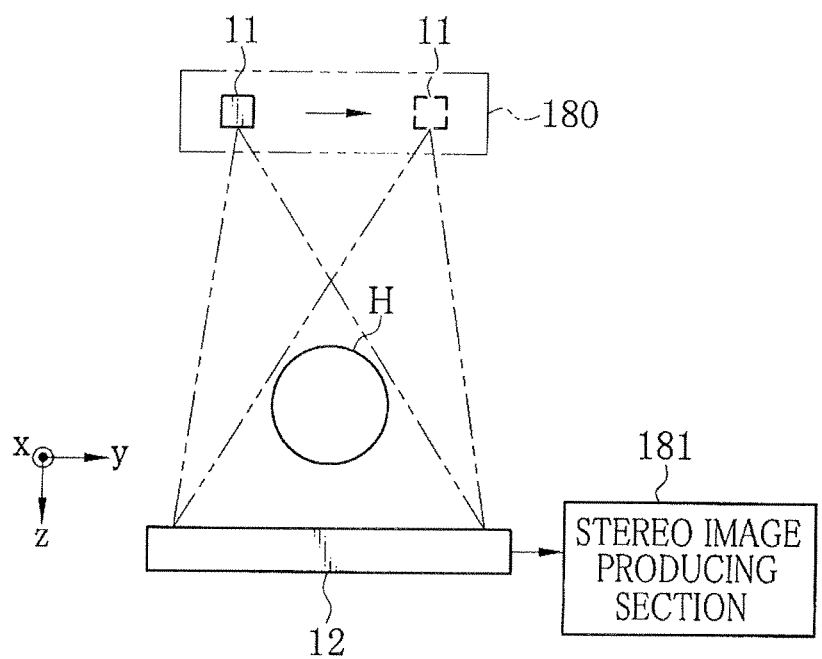
FIG. 30 is a schematic diagram showing a stereoscopic apparatus according to a 15th embodiment of the present invention.

To separate the obstruction shadow and to allow correct image interpretation and diagnosis, it is preferable to apply the present invention to a stereoscopic apparatus for obtaining a stereo image allowing stereoscopic vision. To be more specific, as shown in FIG. 30, a position changing mechanism 180 for changing a position of the X-ray source 11 relative to the object H and the imaging unit 12 in the direction of the arrow in the FIG. 30 is provided. Based on two phase contrast images of the object H obtained by the imaging unit 12 at the first and second positions changed by the position changing mechanism 180, a stereo image producing section 181 produces a stereo image of the object H.

In the first and second positions, it is preferable to adjust the collimator 19a such that the X-ray irradiation area of the X-ray source 11 coincides with the imaging section 41 of the imaging unit 12. It is preferable to coincide the X-ray irradiation area and the imaging section 41 by changing the angle of the X-ray source 11 in the first and second positions.

A method for producing a stereo image based on two images is similar to or the same as the conventional stereoscopic apparatus. In this embodiment, as with the fifth embodiment, the object H may be arranged between the first absorption grating and the second absorption grating. Instead of the X-ray source 11, the X-ray source 121 of the 8th embodiment may be used. It is preferable to use the FPD 160 of the $12^{th}$ embodiment to obtain one phase contrast image by single exposure.

In this embodiment, because the position of the X-ray source 11 is changed along the y direction (the extending directions of the X-ray shield members of the first and second absorption gratings), there is an advantage that the shadowing due to inclined incident of the X-ray on the first and second absorption gratings by the position changes of the X-ray source 11 does not occur.

16th Embodiment

The conventional X-ray diagnostic imaging is based on absorption contrast images. Although the phase contrast image allows the visualization of tissue and its pathological change which have been difficult to visualize in absorption contrast images, the reference to the absorption contrast image corresponding to the phase contrast image assists interpretation. For example, it is effective to compensate the absorption contrast image with information of the phase contrast image by superimposing the absorption contrast image and the phase contrast image with each other through appropriate processes such as weighting, gradation, and frequency enhancement processing. Capturing the absorption contrast image in addition to the phase contrast image, however, makes it difficult to superimpose the phase contrast image and the absorption contrast image due to the displacement of the body site of interest during the image capture of the phase contrast image and the absorption contrast image. Moreover, increasing the number of image capture increases the physical stress of the object (patient). Recently, small angle scattering images have attracted attention in addition to the phase contrast image and the absorption contrast image. A small angle scattering image is capable of representing tissue conditions resulting from microstructure inside the tissue. Small angle scattering image is expected as a method for representation used for new image diagnoses of cancers, cardiovascular diseases, and the like.

Figure 31:
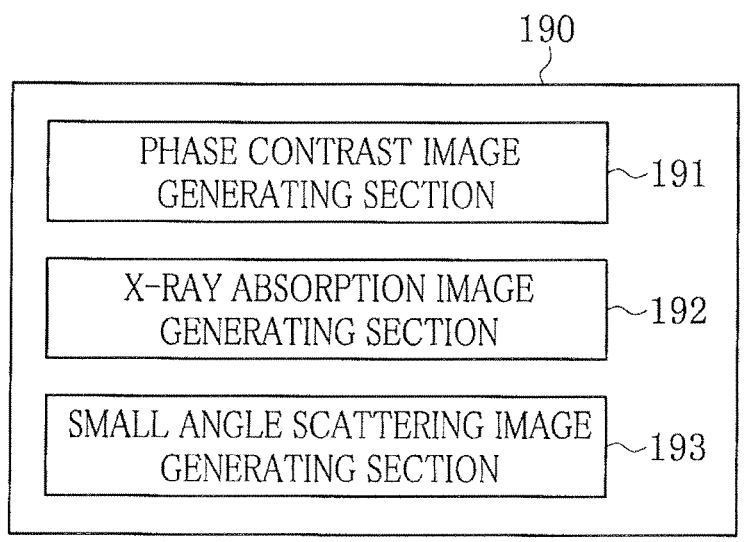
FIG. 31 is a block diagram of a processing section used in the 16th embodiment of the present invention.

In this embodiment, as shown in FIG. 31, a processing section 190 capable of generating an absorption contrast image and a small angle scattering image based on two or more images obtained for producing a phase contrast image is used. The processing section 190 is composed of a phase contrast image generating section 191, an absorption contrast image generating section 192, a small angle scattering image generating section 193. These sections perform processing based on image data obtained at each of the M pieces of the scanning positions where k=0, 1, 2, . . . , and M−1. Of these sections, the phase contrast image generating section 191 generates a phase contrast image following the above described procedures.

Figure 32:
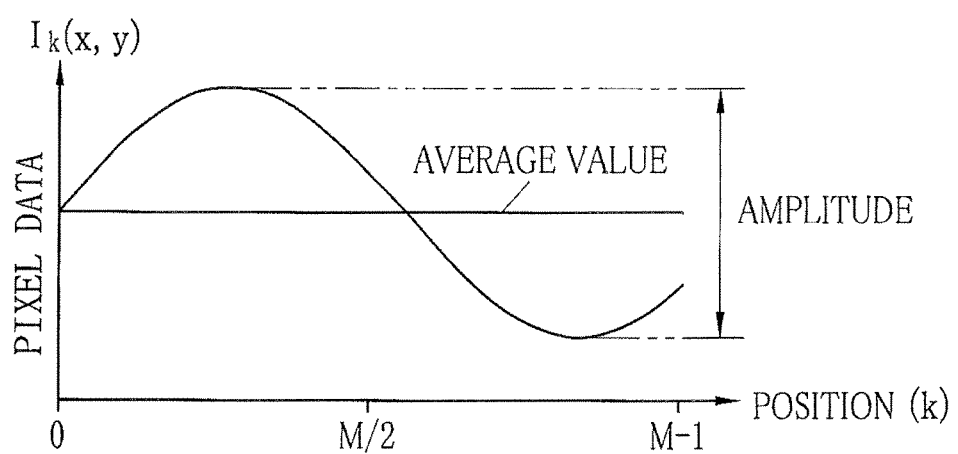
FIG. 32 is a graph describing a method for generating an absorption contrast image and a small angle scattering image.

As shown in FIG. 32, the absorption contrast image generating section 192 generates an absorption contrast image by average values calculated for the each pixel data $I_k$ (x, y) for all or apart of k section. The average value may be calculated simply by averaging the pixel data $I_k$ (x, y) with respect to k. However, When M is small, the resultant absorption contrast image includes relatively large deviation error. In this case, after the pixel data $I_k$ (x, y) may be fitted with a sine wave, the average value of the fitted sine wave may be obtained. Values other than the average value can be used for the generation of the absorption contrast image if the value corresponds to the average value. So values in which the pixel data $I_k$ (x, y) are simply added for all or a part of k section in each pixel can be used.

The small angle scattering image generating section 193 generates a small angle scattering image by amplitude values of the pixel data $I_k$ (x, y) for all or a part of k section in each pixel. The calculation of the amplitude value may be performed by obtaining a difference between a maximum value and a minimum value of the pixel data $I_k$ (x, y) for all or a part of k section. If the "M" is small, the resultant small scattering image includes relatively large deviation errors. In this case, an amplitude value of the fitted sine wave may be obtained after the pixel data $I_k$ (x, y) is fitted using a sine wave. Other than the amplitude value, to generate a small angle scattering image, a variance, a standard deviation, and the like can be used as a value corresponding to variation relative to the average value.

17th Embodiment

In the above-described first embodiment, the X-ray source 11 for emitting the X-ray in cone beam is used as an example. Instead, the X-ray source for emitting X-ray in parallel beams can be used. In this case, the above mathematical expression (1) is changed to a mathematical expression (22). The above mathematical expression (2) is changed to a mathematical expression (23). The above mathematical expression (3) is changed to a mathematical expression (24). The above mathematical expression (4) is changed to a mathematical expression (25).

$$p_2 = p_1 \tag{22}$$

$$d_2 = d_1 \tag{23}$$

$$Z = m\frac{p_1^2}{\lambda} \tag{24}$$

$$L_2 < \frac{p_1^2}{\lambda} \tag{25}$$

In the above embodiments, the distance $L_2$ between the first absorption grating and the second absorption grating is smaller than the minimum Talbot length. The present invention is not limited to the above. The distance $L_2$ may be equal to or larger than the minimum Talbot length. The distance $L_2$ may be equal to the Talbot length. In the present invention, the X-ray is projected without diffraction by the first absorption grating. The displacement amount Δx (see FIG. 9) increases as the distance $L_2$ increases. Accordingly, the refraction angle ϕ of the X-ray is detected with high accuracy by increasing the distance $L_2$.

In the above embodiments, a phase differential image is obtained using a fringe scanning method. The present invention is not limited to the above. A phase differential image may be obtained using a Fourier transform method disclosed in PCT Publication No. WO2010/050483. In this case, the arrangement pitch and the pixel dimension (the dimension of the X-ray imaging area) of pixels in a direction orthogonal to the moiré fringes need to be different from the moiré period in order to detect the moiré fringes.

INDUSTRIAL APPLICABILITY

The present invention is applied to apparatuses for medical diagnoses. The present invention is not limited to the use for the medical diagnoses. The present invention can be applied to industrial use and radiation detection apparatuses used for non-destructive inspection and the like. Instead of the X-ray, gamma rays and the like can be used as the radiation.

The invention claimed is:

1. A radiation imaging system comprising:
   a first grating having two or more radiation shield members extending in a first direction and arranged at a first pitch in a second direction orthogonal to the first direction, radiation emitted from a radiation source passing through the first grating to generate a first periodic pattern image;
   a second grating having two or more radiation shield members extending in a first direction and arranged at a second pitch in the second direction, the radiation shield members of the second grating partly shielding the first periodic pattern image to generate a second periodic pattern image;
   a scanning section for moving at least one of the first grating and the second grating relative to the other in the second direction at a predetermined pitch;
   a radiation image detector for detecting the second periodic pattern image as an image signal;
   a processing section for imaging phase information based on the image signal obtained by the radiation image detector;
   wherein a mathematical expression $D_X \neq n \times (p_1' \times p_2')/|p_1' - p_2'|$ is satisfied where $p_1'$ denotes a period of the first periodic pattern image relative to the second direction at a position of the second grating, and $p_2'$ denotes a substantial grating pitch of the second grating relative to the second direction, and $D_X$ denotes a dimension of a radiation imaging area of each pixel in the radiation image detector relative to the second direction, and n denotes a positive integer.

2. The radiation imaging system of claim 1, wherein a mathematical expression $D_X < (p_1' \times p_2')/|p_1' - p_2'|$ is satisfied.

3. The radiation imaging system of claim 1, wherein the first grating is an absorption grating, and the radiation passed through the first grating forms the first periodic pattern image as a project image without causing Talbot interference.

4. The radiation imaging system of claim 3, wherein a mathematical expression $L_2 < \{(L_1+L_2)/L_1\} \times p_1^2/\lambda$ is satisfied where $L_1$ denotes a distance between a focal point of the radiation source and the first grating, $L_2$ denotes a distance between the first grating and the second grating, $p_1$ denotes the first pitch, and $\lambda$ denotes a peak wavelength of the radiation.

5. The radiation imaging system of claim 1, wherein a mathematical expression $p_2 = \{(L_1+L_2)/L_1\} \times p_1$ is satisfied where $L_1$ denotes a distance between a focal point of the radiation source and the first grating, $L_2$ denotes a distance between the first grating and the second grating, $p_1$ denotes the first pitch, and $p_2$ denotes the second pitch.

6. The radiation imaging system of claim 1, wherein a mathematical expression $d_2 = \{(L_1+L_2)/L_1\} \times d_1$ is satisfied where $L_1$ denotes a distance between a focal point of the radiation source and the first grating, $L_2$ denotes a distance between the first grating and the second grating, $d_1$ denotes an opening width of a slit of the first grating in the second direction, and $d_2$ denotes an opening width of a slit of the second grating in the second direction.

7. The radiation imaging system of claim 6, wherein a mathematical expression $h_1 \leq \{L/(V/2)\} \times d_1$ is satisfied where L denotes a distance between the focal point of the radiation source and the radiation image detector, and $h_1$ denotes thickness of the radiation shield member, of the first grating, in a direction orthogonal to the first and second directions, and V denotes a length of an effective field of view in the second direction at a detection surface of the radiation image detector.

8. The radiation imaging system of claim 7, wherein a mathematical expression $h_2 \leq \{L/(V/2)\} \times d_2$ is satisfied where $h_2$ denotes thickness of the radiation shield member of the second grating in a direction orthogonal to the first and second directions.

9. The radiation imaging system of claim 1, further including a radiation source having a third grating for shielding the radiation in an area-selective manner to generate a plurality of point light sources, wherein a position of the third grating is regarded as a position of the focal point.

10. The radiation imaging system of claim 1, wherein the radiation image detector is a flat panel detector in which pixels are arranged in two dimensions along the first and second directions.

11. The radiation imaging system of claim 1, further including a changing section for changing at least one of the period $p_1'$ and the pitch $p_2'$.

12. The radiation imaging system of claim 11, wherein the changing section rotates at least one of the first grating and the second grating about a rotation axis parallel to a direction orthogonal to the first and second directions.

13. The radiation imaging system of claim 11, wherein the changing section inclines at least one of the first grating and the second grating about a rotation axis parallel to the first direction.

14. The radiation imaging system of claim 11, wherein the changing section moves at least one of the first grating and the second grating in a direction orthogonal to the first and second directions.

15. The radiation imaging system of claim 1, wherein the phase information is a phase differential image generated by calculating a phase shift value of an intensity modulated signal, and the intensity modulated signal is obtained in each pixel of the radiation image detector.

16. The radiation imaging system of claim 15, wherein the processing section integrates the phase differential image in the second direction to generate a phase contrast image.

17. The radiation imaging system of claim 1, further including a grating rotation section for rotating the first grating and the second grating at a predetermined angle about a rotation axis parallel to a direction orthogonal to the first and the second directions, wherein the phase information is imaged before and after the rotation.

18. The radiation imaging system of claim 1, wherein the radiation source and the radiation image detector are horizontally opposed to allow imaging of an object in a standing position.

19. The radiation imaging system of claim 1, wherein the radiation source and the radiation image detector are opposed in the up-and-down direction to allow imaging of an object in a lying position.

20. The radiation imaging system of claim 1, wherein a rotary arm holds the radiation source and the radiation image detector to allow imaging of an object in a standing position and a lying position.

21. The radiation imaging system of claim 1, wherein the radiation imaging system is a mammography apparatus allowing imaging of a breast as an object.

22. The radiation imaging system of claim 21, further including an interlocking movement section for moving the radiation source, the first grating, the intensity modulator, and the radiation image detector in an interlocking manner in an optical axis direction relative to the object, and a controller for controlling the interlocking movement section according to a magnification to adjust a distance between the radiation source and the object.

23. The radiation imaging system of claim 21, further including an image detector moving section for moving the radiation image detector relative to the object in an optical axis direction, and a controller for on ling the image detector moving section according to a magnification to adjust a distance between the radiation source and the radiation image detector.

24. The radiation imaging system of claim 1, wherein the first grating and the second grating are arranged along a cylindrical surface having a line passing through a focal point of the radiation source as an axis.

25. The radiation imaging system of claim 24, wherein the first grating and the second grating extend along a direction of a curve of the cylindrical surface.

26. The radiation imaging system of claim 1, further including a rotational movement section for integrally moving the radiation source, the first grating, the second grating, and the radiation image detector about an object, and a three dimensional image producing section for producing a three dimensional image based on two or more pieces of phase information obtained at different rotation angles rotated by the rotational movement section.

27. The radiation imaging system of claim 1, further including a position changing section for changing a relative position between the radiation image detector and the radiation source in the first direction, and a stereo image producing section for producing a stereo image based on the phase information obtained at first and second relative positions changed by the position changing section.

28. The radiation imaging system of claim 1, further including an absorption contrast image generating section for obtaining a value related to an average value of pixel data for each pixel in the radiation image detector to generate an absorption contrast image.

29. The radiation imaging system of claim 1, further including a small angle scattering image generating section for obtaining a value related to variation from the average value of pixel data for each pixel in the radiation detector to generate a small angle scattering image.

* * * * *